US010575521B2

(12) United States Patent
Hernandez-Brenes et al.

(10) Patent No.: US 10,575,521 B2
(45) Date of Patent: Mar. 3, 2020

(54) ANTIMICROBIAL, ANTIBACTERIAL AND SPORE GERMINATION INHIBITING ACTIVITY FROM AN AVOCADO EXTRACT ENRICHED IN BIOACTIVE COMPOUNDS

(71) Applicants: INSTITUTO TECNOLOGICO Y DE ESTUDIOS SUPERIORES DE MONTERREY, Monterrey (MX); AVOMEX, INC., Fort Worth, TX (US)

(72) Inventors: Carmen Hernandez-Brenes, Monterrey (MX); Maria Isabel Garcia-Cruz, Monterrey (MX); Janet Alejandra Gutierrez-Uribe, Monterrey (MX); Jorge Alejandro Benavides-Lozano, Monterrey (MX); Dariana Graciela Rodriguez-Sanchez, Monterrey (MX)

(73) Assignee: INSTITUTO TECHNOLOGICO Y DE ESTUDIOS SUPERIORES DE MONTERREY, Monterrey, Nuevo León (MX)

( * ) Notice: Subject to any disclaimer, the term of this patent is extended or adjusted under 35 U.S.C. 154(b) by 708 days.

(21) Appl. No.: 15/148,712

(22) Filed: May 6, 2016

(65) Prior Publication Data
US 2016/0249613 A1    Sep. 1, 2016

Related U.S. Application Data

(63) Continuation of application No. 13/763,262, filed on Feb. 8, 2013, now abandoned, which is a continuation of application No. PCT/IB2011/053535, filed on Aug. 9, 2011.

(60) Provisional application No. 61/371,984, filed on Aug. 9, 2010.

(51) Int. Cl.
| | | |
|---|---|---|
| *A01N 37/12* | (2006.01) | |
| *A61K 45/06* | (2006.01) | |
| *A61K 36/54* | (2006.01) | |
| *A01N 65/24* | (2009.01) | |
| *A23L 3/3499* | (2006.01) | |
| *A61K 8/37* | (2006.01) | |
| *A61K 31/22* | (2006.01) | |
| *A61Q 19/00* | (2006.01) | |
| *C07C 69/145* | (2006.01) | |
| *C07C 69/16* | (2006.01) | |
| *C11D 3/20* | (2006.01) | |

(52) U.S. Cl.
CPC .............. *A01N 37/12* (2013.01); *A01N 65/24* (2013.01); *A23L 3/3499* (2013.01); *A61K 8/37* (2013.01); *A61K 8/375* (2013.01); *A61K 31/22* (2013.01); *A61K 36/54* (2013.01); *A61K 45/06* (2013.01); *A61Q 19/00* (2013.01); *C07C 69/145* (2013.01); *C07C 69/16* (2013.01); *C11D 3/2093* (2013.01); *A23V 2002/00* (2013.01); *A61K 2236/33* (2013.01); *A61K 2236/35* (2013.01); *A61K 2800/524* (2013.01)

(58) Field of Classification Search
CPC ...................................................... A61K 36/54
USPC ................................................. 424/725, 777
See application file for complete search history.

(56) References Cited

U.S. PATENT DOCUMENTS

| | | | |
|---|---|---|---|
| 2,550,254 A | 4/1951 | Jensen | |
| 5,217,950 A | 6/1993 | Blackburn et al. | |
| 5,458,876 A | 10/1995 | Monticello | |
| 5,468,490 A | 11/1995 | Huber et al. | |
| 5,498,411 A * | 3/1996 | Rancurel | A61K 8/922 426/417 |
| 5,573,797 A | 11/1996 | Wilhoit | |
| 5,573,800 A | 11/1996 | Wilhoit | |
| 5,573,801 A | 11/1996 | Wilhoit | |
| 6,057,366 A | 5/2000 | Seawright et al. | |
| 6,133,313 A * | 10/2000 | Thomson | A01N 37/12 514/461 |
| 6,326,364 B1 | 12/2001 | Lin et al. | |
| 6,582,688 B1 | 6/2003 | Broutin et al. | |
| 6,620,446 B2 | 9/2003 | King et al. | |
| 7,101,913 B2 | 9/2006 | Arimoto et al. | |
| 7,862,842 B2 | 1/2011 | Beltran et al. | |
| 9,422,504 B2 | 8/2016 | Msika et al. | |
| 9,962,344 B2 | 5/2018 | Baron et al. | |
| 2004/0122095 A1 | 6/2004 | Bonaventura et al. | |
| 2005/0170027 A1 | 8/2005 | Arimoto et al. | |
| 2006/0062813 A1 | 3/2006 | Adachi et al. | |
| 2006/0099323 A1 | 5/2006 | Piccirilli et al. | |

(Continued)

FOREIGN PATENT DOCUMENTS

| | | |
|---|---|---|
| CA | 494110 A | 6/1953 |
| GB | 1421129 A | 1/1976 |

(Continued)

OTHER PUBLICATIONS

Valeri et al., "Phytochemical and Toxicological Study of Pericarp of the Avocado Pear," Rev. Med. Vet. Parasitol (Maracay) vol. 13, pp. 37-58 (1954).

International Preliminary Report on Patentability and Written Opinion for corresponding International Application No. PCT/IB2011/053535 (dated Feb. 12, 2013).

International Search Report and Written Opinion for corresponding International Application No. PCT/IB2011/053535 (dated Aug. 3, 2012).

(Continued)

*Primary Examiner* — Michael Barker
(74) *Attorney, Agent, or Firm* — Pepper Hamilton LLP

(57) ABSTRACT

The present disclosure relates to extracts from *Persea* sp. (avocado) enriched in bioactive compounds which can be used as antimicrobial, antibacterial or spore germination inhibiting agents, the process for obtaining the extracts, acetogenins and isolated molecules and methods for using the extracts enriched in bioactive compounds for providing antimicrobial, antibacterial or spore germination inhibiting effect.

43 Claims, 10 Drawing Sheets

(56) References Cited

U.S. PATENT DOCUMENTS

| | | | |
|---|---|---|---|
| 2009/0163590 A1 | 6/2009 | Msika et al. |
| 2010/0034944 A1 | 2/2010 | Beyazova et al. |
| 2011/0217521 A1 | 9/2011 | Meretzki et al. |
| 2011/0250154 A1 | 10/2011 | Meretzki et al. |
| 2012/0071551 A1 | 3/2012 | Mesina et al. |
| 2012/0201884 A1 | 8/2012 | Gokuraju et al. |
| 2012/0294887 A1 | 11/2012 | Saunois et al. |

FOREIGN PATENT DOCUMENTS

| | | | |
|---|---|---|---|
| JP | 2001097828 A | 10/2001 |
| JP | 2002053474 A | 2/2002 |
| JP | 2003509506 A | 11/2003 |
| JP | 2008156240 A | 7/2008 |
| JP | 2009164558 A | 7/2009 |
| WO | 9522969 A1 | 8/1953 |
| WO | 2010/00744 A2 | 1/2010 |
| WO | 2010026596 A2 | 3/2010 |

OTHER PUBLICATIONS

Office Action for Canadian Patent Application No. 2,807,779 dated Oct. 2, 2017.

Office Action for European Application No. 14176098.3-1454 dated Dec. 13, 2017.

Office Action for Philippines Patent Application No. 1/2013/500258 dated Jan. 5, 2018.

Carman et al., "A Further Synthesis of an Analogue of the Antifungal/Antiherbivore Lipid and Avocado," Aust. J. Chem. 51:955-959 (1998).

Restriction Requirement for U.S. Appl. No. 13/763,262 dated Mar. 3, 2015.

Office Action for U.S. Appl. No. 13/763,262 dated Jun. 5, 2015.

Office Action for U.S. Appl. No. 13/763,262 dated Jan. 6, 2016.

Ciarciaglini et al., "Germination-Induced Bioluminescence, a Route to Determine the Inhibitory Effect of a Combination Preservation Treatment on Bacterial Spores," Applied and Envirmonmental Microbiology 66(9):3735-3742 (2000).

Heyndrickx, M., "The Importance of Endospore-Forming Bacteria Originating from Soil for Contamination of Industrial Food Processing," Applied and Environmental Soil Science 2011 Article ID 561975 11 pages (2011).

Prusky et al., "Identification of an Antifungal Compound in Unripe Avocado Fruits and its Possible Involvement in the Quiescent Infections of Colletotrichum Gloeosporioides," J. Phytopathology 132: 319-327 (1991).

Jackson et al., "Survival and Growth of Clostridium perfringens in Commercial No-Nitrate-or-Nitrite-Added (Natural and Organic) Frankfurters, Hams, and Bacon," Journal of Food Protection 74:3 410-416 (2011).

Knapp et al., "Bactericidal Effects of Polyunsaturated Fatty Acids," The Journal of Infectious Diseases 154:1 84-94 (1986).

Slepecky R. and Hemphill E., "The Genus *Bacillus*-Nonmedical," pp. 530-562 in the Prokaryotes (M. Dworkin, S. Falkow, E. Rosenberg, K. Schleifer, and E. Stackenbrandt eds., 3d ed. 2006).

Chen et al., "Bacteriocins and Their Food Applications," Comprehensive Reviews in Food Science and Food Safety 2(3):82-100 (2003).

Davidson et al., "Antimicrobials in Food," Third Edition, CRC Press, Taylor & Francis Group, Boca Raton, Florida (2005).

Hara-Kudo et al., "Antibacterial Action on Pathogenic Bacterial Spore by Green Tea Catechins," Journal of the Science of Food and Agriculture 85:2354-2361 (2005).

Pierson et al., "Nitrite, Nitrite Alternatives, and the Control of Clostridium Botulinum in Cured Meats," Critical Reviews in Food Science and Nutrition 17(2):141-187 (1983).

Tsukiyama et al., "Antibacterial Activity of Licochalcone A Against Spore-Formng Bacteria," Antimicrobial Agents and Chemotherapy 46(5):1226-1230 (2002).

Castillo-Juarez et al., "Anti-Helicobacter Pylori Activity of Plants Used in Mexican Traditional Medicine for Gastrointestinal Disorders," J. Ethnopharmacol. 122:402-405 (2009).

Hurtado et al., "*Staphylococcus aureus*: Revision of the Mechanisms of Pathogenicity and Physiopathology of Staphylococcal Infections," Rev. Soc. Venez. Microbiol. 22:112-118 (2002) (abstract only).

Leite et al., "Chemical Composition, Toxicity and Larvicidal and Antifungal Activities of *Persea americana* (Avocado) Seed Extracts," Rev. Soc. Bras. Med. Trop. 42(2):110-113 (2009).

Prusky et al., "The Relationship Between Antifungal Diene Levels and Fungal Inhibition During Quiescent Infection of Unripe Avocado Fruits by Colletotrichum gloeosporioides," Plant Pathol. 40:45-52 (1991).

Raymond-Chia et al., "Antimicrobial Activity of Crude Epicarp and Seed Extracts from Mature Avocado Fruit (*Persea americana*) of Three Cultivars," Pharm. Biol. 48:753-756 (2010).

Sivanathan et al., "Biological Activity of Four Antifungal Compounds in Immature Avocado," J. Phytopat. 125:97-109 (1989).

Notice of Reasons for Rejection for Japanese Patent Application 2013-523692 dated Jul. 12, 2016.

Medicinal Chemistry of Natural Products, Nankodo Co., Ltd., pp. 139-141 (2004).

Prusky et al., "Regulation of Natural Resistance of Avocado Fruit for the Control of Postharvest Disease," Proc. of Second World Avocado Congress, pp. 479-484 (1992).

Rodriguez-Sanchez et al., "Isolation and Chemical Identification of Lipid Derivatives from Avocado (*Persea americana*) Pulp with Antiplatelet and Antithrombotic Activities," Food Function 6:193-203 (2015).

International Search Report and Written Opinion dated Apr. 21, 2016 in PCT/IB2015/002021.

Subsequent Substantive Examination Report for Philippines Patent Application No. 1/2013/500258 dated Jan. 30, 2017.

International Search Report, PCT/IB2011/053535, dated Aug. 3, 2012, 4 pages.

Yang, H., et al., "Supercritical fluid CO2 extraction and simultaneous determination of eight annonaceous acetogenins in *Annona* genus plant seeds by HPLC-DAD method," Journal of Pharmaceutical and Biomedical Analysis, vol. 49, (2009), pp. 140-144.

Ugbogu, O.C., et al., "Short Communication: The antimicrobial effect of oils from Pentaclethra macrophylla Bent, Chrysophyllum albidum G Don and Persea gratissima Gaerth F on some local clinical bacteria isolates," African Journal of Biotechnology, vol. 8 (2), pp. 285-287, Jan. 19, 2009.

Sugiyama, T., et al., "Synthesis of All Four Stereoisomers of Antibacteria Component of Avocado," Agric. Biol Chem., vol. 46 (2), pp. 481-485 (1982).

Smola, M., Thesis, "Contribution a l'etude de la formulation et de l'analyse physiochimique de formulations pediatriques microemulsionnees," Unviersite Louis Pastuer Strasbourg I, 2007, 297 pages (English portions included within text).

Rodriguez-Saona, C., et al., "Growth Inhibitory, Insecticidal, and Feeding Deterrent Effects of (12Z, 15Z)-1-Acetoxy-2-Hydroxy-4-Oxo-Heneicosa-12, 15-Diene, A Compound from Avocado Fruit to Spodoptera exigua," Journal of Chemical Ecology, vol. 23, No. 7, (1997), 13 pages.

Rodriguez Carpena, J-G, et al. "Avocado (*Persea americana* Mill.) Phenolics, In Vitro Antioxidant and Antimicrobial Activities, and Inhibition of Lipid and Protein Oxidation in Porcine Patties," Journal of Agricultural and Food Chemistry, vol. 59, (2011), pp. 5625-5635.

Rayman, M.K., et al., "Nisin: a Possible Alternative or Adjunct to Nitrite in the Preservation of Meats," Applied and Environmental Microbiology, vol. 41, No. 2, Feb. 1981, pp. 375-380.

Ramos-Jerz, M., et al., Dissertation, Phytochemical Analysis of Avocado Seeds (*Persea americana* Mill., C.v. Hass), published by Cuvillier Verlag, Oct. 16, 2007, 159 pages.

Prusky, D., et al., "Possible Involvement of an Antifungal Diene in the Latency of Colletotrichum gloeosporioides on Unripe Avocado Fruits," Phytopathotogy, Vo 72, pp. 1578-1582 (1982).

(56) References Cited

OTHER PUBLICATIONS

Padron, J.M., et al., "Beta-Hydroxy-alpha. Beta-unsaturated ketones: A new Pharmacophore for the design of anticancer drugs," Bioorganic & Medicinal Chemistry Letters, vol. 16, (2006), pp. 2266-2269.
Oberlies, N.H., et al., "Cytotoxic and Insecticidal Constituents of the Unripe Fruit of Persea americana," J. Nat. Prod., vol. 61, (1998), pp. 781-785.
Neeman, I., et al., "New Antibacterial Agent Isolated from the Avocado Pear," Applied Microbiology, vol. 19, No. 3, Mar. 1970, pp. 470-473.
Murakoshi, S., et al., "Effects of Two Components from the Avocado Leaves (Perseea americana Mill.) and the Related Compounds on the Growth of Silkworm Larvae, Bombyx mori L.," Jap. J. appl. Ent. Zool. vol. 20, pp. 87-91, (1976), Abstract in English.
Maseko, R.B., "Synthesis of Authentic Organic Standards of Antibacterial Compounds Isolated from Avocados," Dissertation, Department of Chemistry and Physics Faculty of Natural Sciences, Tshwane University of Technology, May 2006, 106 pages.
MacLeod, J.K., et al., "A Short Enantioselective Synthesis of a Biologically Active Compound from Persea Americana" Journal of Natural Products, vol. 58, No. 8, pp. 1270-1273, Aug. 1995.
Leon, L.G. et al., "beta-Hydroxy-alpha, beta-unsaturated ketones. A new pharmacophore for the design of anticancer drugs, Part 2," ChemMedChem, vol. 3, (2008), pp. 1740-1747.
Kim, O.K., et al., "Novel Nitric Oxide and Superoxide Generation Inhibitors, Persenone A and B, from Avocado Fruit," J Agric Food Chem , vol. 48, (2000), pp. 1557-1563.
Kim, O.K. et al, "Inhibition by (−)-Persenone A-related Compounds of Nitric Oxide and Superoxide Generation from Inflammatory Leukocytes," Biosci Biotechnol Biochem , vol. 64, No. 1, pp. 2500-2503 (2000).
Kim, O.K , et al., An Avocado Constituent, Persenone A, Suppresses Expression of Inducible Forms of Nitric Oxide Synthase and Cyclooxygenase in Macrophages, and Hydrogen Peroxide Generation in Mouse Skin, Biosci. Thotechnol. Biochem., vol. 64, No. 11, p. 2504-2507 (2000).
Kashman, Y., et al , "New Compounds from Avocado Pear," Tetrahedron, vol. 25, pp. 4617-4631, Pergamon Press, (1969).
Kabuki, T. et al., "Characterization of novel antimicrobial compounds from mango (Mangifera indica L.) kernel seeds," Food Chemistry, vol. 71, pp. 61-66, (2000).
Hashimura, H. et al., "Acetyl-CoA Carboxylase Inhibitors from Avocado (Persea americana Mill) Fruits," Biosci. Biotechnol. Biochem., vol. 65, No. 7, pp. 1656-1658 (2001).
Greene, T.W. et al., "Protective Groups in Organic Synthesis," Third Edition, Chapter 1: The Role of Protective Groups in Organic Synthesis, 16 pages (1999).
Foucault, A.P. et al., "Counter-current chromatography: instrumentation, solvent selection and some recent applications to natural product purification," Journal of Chromatography A., vol. 808, pp. 3-22 (1998).
Domergue, F. et al , "Antifungal compounds from idioblast cells isolated from avocado fruits," Phytochemistry, vol. 54, pp. 183-189 (2000).
Chia, T.W.R. et al., "Antimicrobial activity of crude epicarp and seed extracts from mature avocado fruit (Persea americana) of three cultivars," Pharmaceutical Biology, vol. 48, No. 7, pp. 753-756 (2010).
Chang, C-F, et al., "Isolation and Structure Elucidation of Growth Inhibitors for Silk-worm Larvae from Avocado Leaves," Short Communication: Agr. Biol. Chem., vol. 38, No. 5, pp. 1167-1168 (1975).
Canadian Food Directorate, Clostridium botulinum Challenge Testing of Ready-to-Eat Foods, Food Directorate, Health Products and Food Branch. Health Canada, Version No. 1, Issue Date. Nov. 24, 2010, 11 pages.
Butt, A.J. et al., "A novel plant toxin, persin, with in vivo activity in the mammary gland, induces Bim-dependent apoptosis in human breast cancer cells," Molecular Cancer Therapeutics, vol. 5, pp. 2300-2309 (2006).
Bull, S.D. et al., "Synthesis of the Avocado Antifungal, (Z,Z)-2-Hydroxy-4-oxohenicosa-12,15-dien-1-yl Acetate," Aust. J Chem , vol. 47, pp. 1661-1672 (1994).
Brown, B.I., "Isolation of Unpleasant Flavor Compounds in the Avocado (Persea americana)," J. Agr. Food Chem., vol. 20, No. 4, 5 pages (1972).
AOAC Official Method 966.04, Sporicidal Activity of Disinfectants, First Action 1966, Final Action 1967, Revised 2002, 6 pages.
Tang. Y., et al , "Inhibition of Food-Borne Pathogens by T1, a Novel Antimicrobial Peptide as a Potential Food Preservative," USDA National Agricultural Library, International Journal of Food Engineering, vol. 4, No. 4, 2008, (Abstract provided).
First Office Action for China Patent Application No. 201180048894.6 dated Jun. 11, 2014.
Second Office Action for China Patent Application No. 201180048894.6 dated Mar. 13, 2015.
Third Office Action for China Patent Application No. 201180048894.6 dated Oct. 26, 2015.
Notice of Reasons for Rejection for Japanese Patent Application 2013-523692 dated Aug. 24, 2015.
Extended European Search Report for European Patent Application No. 11828227.6 dated Dec. 11, 2013.
Partial European Search Report for European Patent Application No. 14176098.3 dated Feb. 2, 2015.
Idris et al., "Preliminary Phytochemical Screening and Antimicrobial Activity of Seed Extracts of Persea americana (Avocado Pear)," Bayero Journal of Pure and Applied Sciences 2(1):173-176 (2009).
Extended European Search Report for European Patent Application No. 14176098.3 dated May 29, 2015.
Rodriguez-Saona et al., "Biologically Active Aliphatic Acetogenins from Specialized Idioblast Oil Cells," Current Organic Chemistry 4:1249-1260 (2000).
Rodriguez-Saona et al., "Isolation, Identification,and Biological Activity of Isopersin, a New Compound from Avocado Idioblast Oil Cells," J. Nat. Prod. 61:1168-1170 (1998).
Nagaraj et al., "Antioxidant and Antibacterial Activity of Avocado (Persea gratissima Gaertner) Seed Extract," World Applied Sciences Journal 9(6):695-698 (2010).
Fourth Office Action for China Patent Application No. 201180048894.6 dated Apr. 18, 2016.
Office Action for Canadian Patent Application No. 2,807,779 dated Jun. 4, 2018.
First Office Action for China Patent Application No. 201610773165.1 dated May 9, 2018 (English Translation).
Office Action for Philippines Patent Application No. 1/2013/500258 dated Jun. 8, 2018.
European Office Action for European Patent Application Serial No. 14176098.3 (dated Jan. 28, 2019).
Chinese Office Action for Chinese Patent Application Serial No. 201610773165.1 (dated Jan. 23, 2019).
Office Action for U.S. Appl. No. 15/348,740 (dated Feb. 11, 2019).
Office Action Restriction Requirement for U.S. Appl. No. 15/580,933 (dated Jul. 5, 2018).
Office Action for U.S. Appl. No. 15/580,933 (dated Nov. 23, 2018).
Karni et al., "Involvement of Epicatechin in the Regulation of Lipoxygenase Activity During Activation of Quiescent Colletotrichum gloeosporioides Infections of Ripening Avocado Fruits," Physiol. Mol. Plant Pathol. 35:367-74 (1989).
Kobiler et al., "Compartmentation of Antifungal Compunds in Oil Cells of Avocado Fruit Mesocarp and its Effect on Susceptibility to Colletotrichum gloesporioides," Physiol. Mol. Plant Pathol. 43:319-28 (1993).
Bittner et al., "Isolation and Identification of a Plant Growth Inhibitor from Avocado," Phytochemistry 10:1417-21 (1971).
Gazit et al., "Inhibitor and Auxin Activity in the Avocado Fruit," Physiol. Plant. 27:77-82 (1972).
Kawagishi et al., "Liver Injury Suppressing Compounds from Avocado (Persea americana)," J. Agric. Food Chem. 49:2215-21 (2001).
Kashman et al, "Six New C17-Olefinic and Acetylenic Oxygenated Compounds from Avocado Pear," Israel J. Chem. 2:173-6 (1969).

(56) References Cited

OTHER PUBLICATIONS

Prusky, "The use of Antioxidants to Delay the Onset of Anthracnose and Stem End Decay in Avocado Fruits after Harvest," Plant Disease 72:381-4 (1988).
Prusky, "Further Evidence for the Involvement of a Preformed Antifungal Compound in the Latency of Colletotrichum Gloeosporioides on Unripe Avocado Fruits," Physiol. Plant Pathol. 22:189-98 (1983).
Third Office Action for China Patent Application Serial No. 201610773165.1 (dated Sep. 25, 2019).
Summons to Attend Oral Proceedings for European Patent Application Serial No. 14176098.3 (dated Oct. 29, 2019).

* cited by examiner

ANTIMICROBIAL, ANTIBACTERIAL AND SPORE GERMINATION INHIBITING ACTIVITY FROM AN AVOCADO EXTRACT ENRICHED IN BIOACTIVE COMPOUNDS

CROSS-REFERENCE TO RELATED APPLICATIONS

This application is a continuation of U.S. patent application Ser. No. 13/763,262, filed Feb. 8, 2013, which is a continuation of International PCT Application No. PCT/IB2011/053535, filed Aug. 8, 2011. This application also claims priority to U.S. Provisional Application No. 61/371,984, filed Aug. 9, 2010. The contents of all of the above are hereby incorporated in their entirety by reference.

Any foregoing applications and all documents cited therein or during their prosecution ("application cited documents") and all documents cited or referenced in the application cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the disclosure.

BACKGROUND

1. Technical Field

Some technical definitions relevant to the disclosure include "non-spore forming bacteria" which is a known term used for pathogenic and spoilage bacteria that cannot form bacterial spores and can be destroyed or controlled by a heat treatment, refrigerated anaerobic storage, antibacterial substances and other methods known in the art used alone or in combination. Another relevant term is "spore forming bacteria", which includes pathogenic and spoilage bacterial capable of forming very resistant structures called bacterial spores (also termed endospores) that are not necessarily destroyed or controlled by the common methods known in the art for the control of non-spore forming bacteria and require specific treatments for their inhibition and/or inactivation. Additionally, both types of bacteria can exist in nature in a "vegetative state" also termed viable cells; however spore-forming bacteria can also exist in a "spore-state" which is more resistant to chemical and physical treatments for their inactivation. In the field of food technologies there are additional bacterial states for spore forming bacteria that are artificially created by the application of heat termed "heat-shocked spores" and/or pressure "pressure-shocked spores". The artificial states generated in the food industry result in an even higher resistance of the spores to their inactivation by chemical and physical means and in some food systems need to be controlled in order to inhibit their germination into the vegetative form of the spore forming bacteria and subsequent spoilage of the food and/or toxin production.

Some additional technical definitions relevant to the disclosure include "antimicrobial" which is a term used to describe an agent able of inhibiting the growth of a wide class of microorganisms including bacterias, fungus, molds, viruses or yeast. Whereas "antibacterial" is a term used to describe an agent able of inhibiting the growth of spore forming or non-spore forming bacterias in a vegetative state. And the term "spore germination inhibiting activity" or "spore germination inhibiting effect" refers to spores from spore forming bacteria, except for where otherwise indicated. Additionally "raw extract" is a term used to define an extract obtained by mixing *Persea* spp. (avocado) tissue with a non-polar or polar solvent and that contains a broad spectrum of chemical compounds other than acetogenins with antimicrobial, antibacterial and spore germination inhibiting effect. Whereas "extract enriched in acetogenins" is the term used to define an extract obtained after the removal of compounds different from acetogenins with antimicrobial, antibacterial and spore germination inhibiting effect.

This disclosure relates to the food and pharmaceutical arts. In particular it relates to a method of inhibiting vegetative cells, spore germination and growth of gram positive bacteria by the use of chemical compounds naturally present in *Persea* spp.

The disclosure also relates to the medical arts. In particular it relates to a method of inhibiting the growth of pathogenic spore forming bacteria in the body including the gastrointestinal tract of a human or non-human vertebrate by the use of an antimicrobial extract with specificity for this type of bacteria.

It is known in the discipline of food processing that food products with pH values>4.6 (commonly known in the food industry as low-acid foods) can experience the germination and growth of spore forming bacteria. Of particular interest for the food industry is the use of food additives capable of inhibiting spore germination and vegetative cell growth from pathogenic spore forming microorganisms such as *Clostridium botulinum, Clostridium perfringens* and *Bacillus cereus*, among others. Under the proper food environments such as enclosed containers or anaerobic conditions generated within the food matrix the spores from these pathogenic microorganisms can germinate and grow to harmful numbers of bacterial cells and in some cases can produce toxins jeopardizing human health. Particularly, the proteolytic and non-proteolytic strains of *Clostridium botulinum* are a major concern for the food industry because of the potential germination of their bacterial spores in foods and the production of potent neurotoxins. Nitrites are the most commonly used food additives in the food industry to retard/inhibit the growth of spore forming pathogenic bacteria in refrigerated low-acid foods. However, there is a consumer and industrial long standing interest to reduce the utilization of synthetic food additives, particularly nitrite compounds. Other food additives that have been used for the same purposes include nisin (Rayman, 1981), recombinant peptides (Tang et al., 2008), 5-aminosalicylates (Lin and Pimentel, 2001) and ethyl lauroyl arginate (Beltran et al., 2011). Additionally, there have been prior patents and articles related to antimicrobial compounds from natural origin that act against bacterial vegetative cells. Many natural sources have been reported to contain antimicrobial compounds mainly lipophilic, although some hydrophilic compounds have also shown activity. Reports of antimicrobial compounds of this nature are available in literature.

The disclosure also relates to an important public health concern that is the ability of pathogenic species, especially the gram positive *Listeria monocytogenes*, to grow at commercial refrigeration temperatures at which processed foods are normally stored before final consumption. *Listeria monocytogenes* is a non-spore forming pathogenic bacteria of special concern for ready-to-eat meats and dairy products; as such foods are frequently not heated by the user prior to consumption. Consumption of foods contaminated with *Listeria monocytogenes* are known in the art to increase the risk of infection, especially among infants, the elderly, pregnant women, and any immune compromised individuals.

For the purposes of this disclosure a sporocidal agent is a substance with the ability to kill at least some types of bacterial spores whereas a sporostatic agent is a substance that has the ability to inhibit the growth and reproduction of at least some types of bacterial spores. Spore germination inhibitors include both sporicidal and sporostatic agents.

In addition, except for where otherwise indicated, depictions of the compounds described below are intended to encompass all stereoisomeric forms thereof which includes (R) and (S) forms and cis (Z) and trans (E) forms of the compounds. For the purposes of this disclosure, the trans (E) form can include a terminal alkene which has the formula —CH=CH$_2$ (see e.g. (2R,16E)-1-acetoxy-2-hydroxy-4-oxo-nonadeca-16,18-diene below).

2. Description of the Related Art

Jensen in 1951 (U.S. Pat. No. 2,550,254) obtained an acetone extract from avocado (*Persea gratissima*) seed having antibacterial activity against vegetative cells from *Staphylococcus aureus, Bacillus subtilis, Aspergillus glaucus, Penicillium notatum*, and *Achromobacter perolens*. This extract was found to be inactive against *Esherichia coli, Pseudomonas fluorescens* and *Penicilliun camemberti*. The same author in 1953 (Canada Patent 494,110) refers to avocado (*Persea americana*) seed as another natural source that might be used to obtain an extract with antimicrobial activity. Valeri and Gimeno (1954) extracted avocado seeds with petroleum ether and reported that the resulting crude wax inhibited growth of *Micrococcus pyogenes* and *Sarcina lutea*, but not growth of *B. subtilis* or of *E. coli*. The prior art indicates that avocado seeds contain antimicrobial compounds but the specific bioactivity of the extract against particular microorganisms clearly depends on the method of extraction, which in the end impacts the chemical composition of the extract.

In the related art, some compounds have been isolated from avocado seed extracts and tested to inhibit the growth of certain microorganisms (bacteria, yeasts and fungi). Kashman et al. (1969) isolated and elucidated the structure of eight compounds from a hexane extract of avocado fruit and seeds and a number of derivates thereof were prepared, obtaining higher yields from the seeds than the fruit. All compounds showed by Kashman (1969) belong to the same group of long chain aliphatic compounds, with one end being unsaturated and the other end highly oxygenated. Interestingly the compounds were divided by the authors in pairs differing only by having a double or triple bond at the end of the chain. The isolation of these compounds was with the aim of performing a chemical characterization and not for obtaining bioactive components (not bioactivity-guided isolation). Additional studies were then performed to evaluate their antimicrobial activity against *Bacillus subtilis, Bacillus cereus, Salmonella typhi, Shigella dysenteriae, Staphylococcus aureus, Candida albicans, Saccharomyces cerevisiae* (ATCC 7752 and S 288C) (Néeman et al. 1970). Only six of twelve long-chain aliphatic compounds tested demonstrated inhibitory effects against some of the microorganisms but only 1, 2, 4-trihydroxy-n-hepadecan-16-en was capable of inhibiting the growth of all the microorganisms included in their study in a disc inhibition antimicrobial test that used 0.05 mg of the compound. The authors concluded that when the hydroxyl groups on the oxidized part of the compound were totally, or partially, acetylated, the antibacterial activity was greatly weakened (Néeman et al. 1970). Therefore acetogenins, which are the acetylated form of the above mentioned long chain aliphatic compounds, did not inhibit the growth of the previously mentioned microorganisms. Baratta et al. (1998) more recently conducted a study to evaluate the antimicrobial and antioxidant properties of an extract of essential oils from plants including laurel (*Laurus nobilis*) form the Lauraceae family but did not include the genus *Persea*.

Recently, Ugbogu and Akukwe (2009) reported on the antimicrobial effects of seed oils from *Persea gratissima* Gaerth F, among other plant seed oils, against clinical isolates of non-spore forming bacteria that included *Escherichia coli, Proteus mirabilis, Pseudomonas aeruginosa, Staphylococcus aureus* and *Staphylococcus epidermis*. The authors reported potential use of *Persea* seed oils in the treatment of wounds. Chia and Dykes (2010) also prepared ethanolic extracts from the epicarp and seed of *Persea Americana* Mill. vars. Hass, Shepard and Fuerte. They reported that at concentrations between 104.2-416.7 μg/ml, the extract showed antimicrobial activities against the growth of vegetative cells of both gram positive and gram negative bacteria; the authors also prepared a water extract that only inhibited the growth of *Listeria monocytogenes* (93.8-375 μg/ml) and *Staphylococcus epidermis* (354.2 μg/ml). Activity against *Clostridium* or *Bacillus* genus was not evaluated for the ethanolic or aqueous extract. Rodriguez-Carpena et al. (2011), in an attempt to isolate molecules with antibacterial activities, prepared extracts from the peel, pulp, and seed of two avocado cultivars (*Persea Americana* Mill.) using three different solvents that included ethyl acetate, acetone (70%) and methanol (70%). The authors tested the antibacterial properties of the extracts against a panel of vegetative cells from non-spore forming and spore forming bacteria, concluding that their antibacterial activity was moderate and it was attributed to the presence of phenolic compounds in their extracts. Therefore the prior cited studies did not successfully performed the isolation or chemical identification of the components potentially responsible for the observed bioactivities or tested bacterial spores, heat-shocked spores or pressure-shocked spores.

Similarly, other authors have tested the antimicrobial properties of the avocado plant, against microorganisms other than bacteria. Prusky et al. (1982) described the presence of 1-acetoxy-2-hydroxy-4-oxo-heneicosa-12,15-diene (Persin) in the peel of unripe avocado fruits and attributed to the molecule the antimicrobial activity against *Colletotrichum gloeosporioides*, a fungus that causes anthracnose, a known problem encountered during storage of avocado fruits. The compound was isolated by Thin Layer Chromatography from an ethanolic extract partitioned with dichloromethane. This compound was later termed "persin" (Oelrichs et al., 1995), and was confirmed by other authors as the constituent of avocado with the highest inhibitory activity against the vegetative growth of the fungi *Colletotrichum gloeosporioides* tested in vitro (Sivanathan and Adikaram, 1989; Domergue et al., 2000), and with the capability to inhibit its fungi spore germination and germ tube elongation (Prusky et al., 1991a). Persin inhibited fungi spore germination completely at 790 μg/ml and the concentration of this compound in the peels was greatly reduced during ripening (Prusky et al., 1982). A monoene with similar structure, 1-acetoxy-2,4-dihydroxy-n-heptadeca-16-ene, also demonstrated bioactivity against *Colletotrichum gloeosporioides* but it was 3 fold lower than that of persin. Interestingly, a 1:1 mixture of both antifungal compounds showed synergistic activity and increased the percent of inhibited germ tube elongation of germinated conidia (Prusky et al., 1991b). Other compounds such as 1-acetoxy-2-hydroxy-4-oxo-heneicosa-5,12,15-triene (Domergue et al., 2000) have also been proven to have antifungal bioactivity. This last compound has been termed "Persenone A" (Kim et al., 2000a), however none of the isolations has been performed based on its bioactivity or with the aim of discovering novel compounds or mixtures with increased bioactivity. Most of the prior art publications have focused on finding molecules to prevent postharvest damage.

Additional bioactivities that have been reported for acetogenins included insecticidal, antitumoral, and antihelmintic properties. Persin has shown to have insecticidal activity, inhibiting the larval feeding of silkworm larvae *Bombyx mori* L., at a concentration in the artificial diet of 200 µg/g or higher (Chang et al., 1975; Murakoshi et al., 1976). More recently, Rodriguez-Saona et al. (1997) demonstrated the effects of persin on *Spodoptera exigua*, a generalist feeder insect, that does not feed on avocados, but is one of the major pests of many vegetables. Inhibitory effects were observed for both larval growth and feeding at concentrations of 200 µg/g and 400 µg/g of diet, respectively.

Persin was also identified as the active principle present in avocado leaves that induces lactating mammary gland necrosis of mice at a dose rate of 60-100 mg/kg, at doses above 100 mg/kg necrosis of mice myocardial fibers may occur, and hydrothorax may be present in severely affected animals (Oelrichs et al., 1995). Derived from this effect, this compound and others obtained from avocado leaves were patented as treatment for ovarian and breast cancer in mammals (Seawright et al., 2000). The compounds were administered orally up to 100 mg/kg of body weight of mammal being treated, but preferably on a number of consecutive days at a concentration of 20-40 mg/kg of body weight to avoid the previously reported toxic effects. As it was previously noted, the concentration of these compounds in the avocado pulp is greatly reduced during ripening to values lower than 1500 µg/g (Kobiler et al, 1993); therefore more than 0.8 kg of avocado pulp should be consumed daily by a 60 kg human to reach the anticancer effect and even a higher concentration to reach the cytotoxic effects. The annual therapeutic dose proposed for cancer treatment is 160-fold higher than the actual annual per capita consumption of avocado in the United States (1.8 kg or 4.1 pounds) reported by Pollack et al (2010).

Persenone A, and its analog 1-acetoxy-2-hydroxy-5-nonadecen-4-one (Persenone B), along with Persin were found to inhibit superoxide (O2$^-$) and nitric oxide (NO) generation in cell culture, activities that were associated by the authors to therapeutic uses as cancer chemopreventive agents in inflammation-related organs (Kim et al., 2000a, 2000b and 2000c). In vitro results demonstrated that they have equal or better activity than DHA (docosahexaenoic acid), a natural NO generation inhibitor. The IC50 values were in the range of 1.2-3.5 µM for acetogenins and 4.5 µM for DHA (Kim et al., 2000a). Additionally, 1-acetoxy-2,4-dihydroxy-n-heptadeca-16-ene, persin and persenone A showed inhibition of acetyl CoA carboxylase (ACC) activity, in the IC50 value range 4.0-9.4 µM (Hashimura, 2001). Authors concluded that since ACC is involved in fatty acids biosynthesis, those compounds have a potential use as fat accumulation suppressors to avoid obesity.

Most of the extraction methods for long-chain fatty acid derivatives require a previous step to recover the oil or the use of organic solvents such as hexane. The method of extraction for the identified antimicrobial compounds used by Kashman, Neeman and Lifshitz, (1969) used hexane at boiling temperatures. Broutin et al. in 2003 (U.S. Pat. No. 6,582,688 B1) developed a method for obtaining an extract from avocado fruit oil enriched in certain class of long chain aliphatic compounds, such as furan lipid compounds and polyhydroxylated fatty alcohols. The authors claimed that different compositions of those non polar compounds may be used in different therapeutic, cosmetic and food applications. However the chemical composition of the extract obtained by their process or the content of the active molecule(s) was not specified for its use as an antimicrobial agent. Considering the toxicity of some of the compounds that might be present in a raw extract, it is extremely important to define the minimal concentration required to attain the desired effects (see U.S. Patent Application Publications 2006-0099323 and 2009-0163590).

Even if some acetogenins have been proven to have antimicrobial activity against vegetative cells of bacteria, the preliminary art does not show any reports on the bio-assay guided isolation of the antimicrobial compounds from avocado (*Persea americana*) against microorganisms, particularly sporulated forms. The present disclosure provides a series of steps for a process to obtain isolated compounds and/or a composition that concentrates the naturally occurring antibacterial compounds in *Persea americana* that inhibit the growth of vegetative and sporulated states of spore forming bacteria. The isolation of compounds based on inhibition of sporulated microorganisms do not form part of the teaching of the prior art. More importantly, the synergistic effect of the specific compounds in partially purified mixtures is also part of the present disclosure. The inventors found intriguing that the partially purified extracts and/or mixtures of isolated compounds possess spore germination inhibiting properties, such as sporostatic and/or sporocidal properties, and in some instances even better effects than the isolated compounds alone. The chemical identity and specificity of the active compounds against spore forming microorganisms has never been previously reported nor the heat or pressure stabilities of the bioactive compounds under commercially applicable processing conditions.

Maseko (2006) proposed a simple method to produce a non acetylated fatty acid derivative called (2R,4R)-1,2,4-trihydroxyheptadeca-16-ene by using (S)-malic acid as a cheap source of the triol fragment and the Grignard reaction to achieve the elongation of the aliphatic chain. This precursor could be used for the synthesis of most acetogenins in avocado oil. This molecule was produced as an analytical standard in Masenko (2006) and in prior art Néeman et al. (1970) had shown the potential of the compound as an antimicrobial agent against *Staphylococcus* spp., a non-spore forming bacteria. None of the cited authors tested any specific antimicrobial properties against spore forming bacteria nor a method to produce acetogenins with this particular effect.

In reference to the prior art on antimicrobial substances to be used for the specific control of vegetative cells of *Listeria monocytogenes* in refrigerated foods, U.S. Pat. No. 5,217,950 suggested the use of nisin compositions as bactericides for gram positive bacteria. U.S. Pat. Nos. 5,573,797, 5,593,800 and 5,573,801 disclose antibacterial compositions which include a combination of a *Streptococcus* or *Pediococcus* derived bacteriocin or synthetic equivalent antibacterial agent in combination with a chelating agent. U.S. Pat. No. 5,458,876 suggests the combination of an antibiotic (such as nisin) with lysozyme as an antibacterial. In this case, lysozyme breaks down the cell wall and weakens the structural integrity of the target cell so that the antibacterial agent becomes more effective in damaging or killing the bacterial cell. In particular, this combination proves to be effective in improving the antibacterial—efficacy of nisin against *Listeria monocytogenes*, yielding a significant reduction, though not a complete elimination, of *Listeria* at safe and suitable levels of use. U.S. Pat. No. 6,620,446B2, describes an antibacterial composition for control of gram positive bacteria in food applications that may be used as an ingredient or applied to a food surface. This composition includes nisin, and/or lysozyme and beta hops acids in order to reduce or eliminate gram positive spoilage or pathogenic bacteria, and, most especially, all strains of the harmful pathogen *Listeria monocytogenes*. Perumalla and Hettiarachchy (2011) reported that green tea extract and grape seed extract (polyphenolic and proanthocyanidin rich compounds) had antimicrobial activities against major food borne pathogens like *Listeria monocytogenes, Salmonella typhimurium, Escherichia coli* O157:H7, and *Campylobacter jejuni*. Furthermore, they have demonstrated synergism in antimicrobial activity when used in combination with organic acids (malic, tartaric acid, benzoic acids etc.), bacteriocins like nisin or chelating agents like EDTA in various model systems including fresh products (fruits and vegetables), raw and ready-to-eat meat and poultry products.

Given the difficulties associated with obtaining extracts with adequate antibacterial, antimicrobial or spore germination inhibiting activities, the development of resistance by bacteria, microbes and spores to known antibacterial, antimicrobial, spore germination inhibiting compounds and compositions, and the desire for food products and medicaments of natural origin, there still exists a need in the art for additional antibacterial, antimicrobial or sporicidal compounds and compositions preferably obtained from economically feasible sources such as plant processing by-products and waste.

BRIEF SUMMARY

This disclosure is directed to an extract enriched in naturally occurring acetogenins from *Persea* spp. characterized by having antimicrobial, antibacterial or spore germination inhibiting effect and the process to obtain the said extract. The disclosure is also directed to the use of the acetogenin enriched extract that presents spore germination inhibiting activity, as a sporicidal and/or sporostatic agent against native bacterial spores from *Clostridium* spp., *Bacillus* spp. and *Alicyclobacillus* spp., among other pathogenic and non-pathogenic bacteria. The disclosure is also directed to pharmaceutical, foods, personal care and cleaning compositions or products comprising the said extract and thus having antimicrobial, antibacterial or spore germination inhibiting effect. We also discovered that the enriched extract is effective as an antimicrobial agent to inhibit the growth of viable cells of other non-spore forming gram positive bacteria such as *Listeria monocytogenes*, in combination with refrigerated conditions. Additionally, we also discovered that the enriched extract contains two natural occurring acetogenins not previously characterized, which have antimicrobial and spore germination inhibiting effect. It is also part of this disclosure to protect the use of the acetogenin enriched extract in formulations that are heat treated, pressure treated or stabilized by other thermal or non-thermal conservation technologies.

Figure 1:
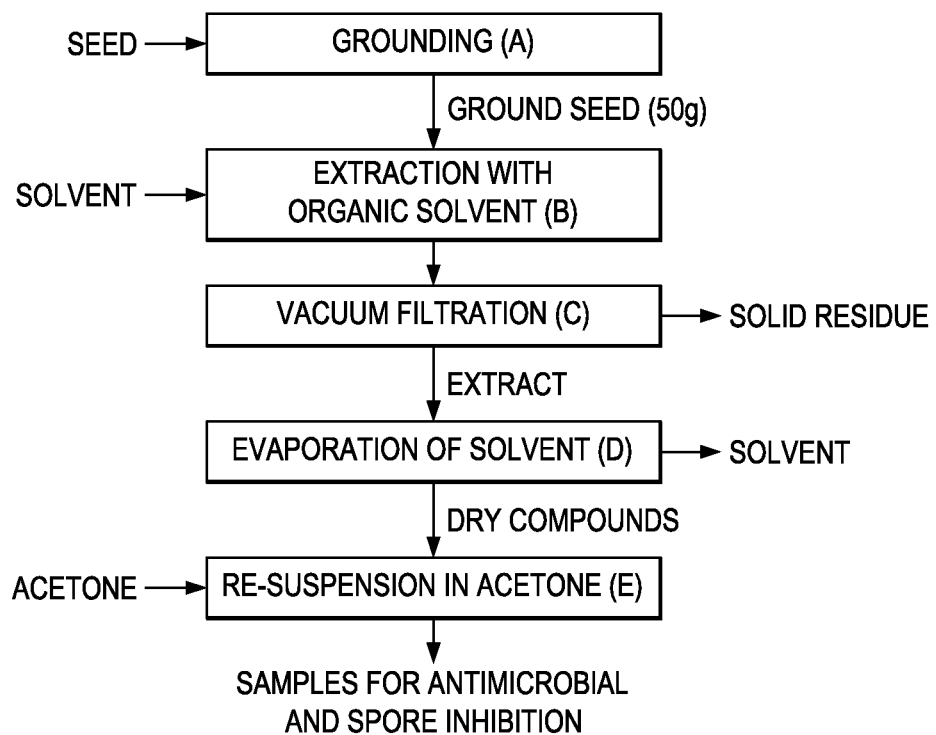
FIG. 1. Primary extraction diagram for the compounds present in avocado seed used to evaluate their antimicrobial activities against vegetative cells, native spores and heat shocked spores of gram positive bacteria.

FIG. 18. Concentration of the active compounds present in the pool of active fractions described in Example 10.

DETAILED DESCRIPTION

The present disclosure provides a series of steps to obtain an extract enriched in naturally occurring antimicrobial, antibacterial or bacterial spore germination inhibiting compounds, termed acetogenins, from *Persea* spp. (avocado) for providing antimicrobial, antibacterial or bacterial spore germination inhibiting effect.

In one aspect of the disclosure is the a process to obtain an extract enriched in naturally occurring acetogenins with antimicrobial, antibacterial or bacterial spore germination inhibiting effect, from *Persea* sp., which includes, but is not limited to *Persea americana* and *gratissima* (avocado) for providing antimicrobial, antibacterial or bacterial spore germination inhibiting effect, which includes but is not limited to the growth of vegetative cells and spores of gram positive bacteria.

In other aspect of the disclosure the process to obtain the said enriched extract has as an starting point a raw extract of the dried or fresh seeds, and/or other *Persea* sp. tissue such as mesocarp, peel, leafstalks, branches or leaves, which comprises:

a) Partitioning of the raw extract serving as an starting point, into a two-phase solvent system to obtain a phase with a high content of acetogenins, further evaporated or concentrated to obtain an extract with a high content of acetogenins;

b) Fractionating the extract with a high content of acetogenins obtained in step a) by Fast or High Performance Centrifugal Partition Chromatography (FCPC or HPCPC) or Countercurrent chromatography (CCC) based on their corresponding partition coefficient, to obtain fractions with higher concentration of acetogenins presenting bacterial spore germination inhibiting effect and separate them from other fractions comprising contaminants;

c) Recovering and mixing of the fractions comprising acetogenins with bacterial spore germination inhibiting effect obtained in step b), and concentration them to finally obtain an extract enriched in naturally occurring acetogenins from *Persea* sp. having bacterial spore germination inhibiting effect.

In one embodiment of this aspect of the disclosure, the two-phase solvent system said in step a) comprises:

at least one polar solvents selected from the group including, but is not limited to water, $C_1$-$C_4$ alcohol (e.g. ethanol, isopropanol, methanol), dimethyl sulfoxide, tetrahydrofuran, acetone, acetonitrile; and at least one non-polar solvents selected from the group including, but is not limited to hexanes, heptanes, ethyl ether, ethyl acetate, petroleum ether, butyl alcohol, chloroform, toluene, methyl tert-butyl ether, methyl isobutyl ketone and mixtures therein.

In another embodiment of this aspect of the disclosure, the fractionation by FCPC, HPCPC or CCC said in step b) is carried out to separate the compounds based on their corresponding partition coefficient with the aim of reducing and/or eliminating contaminants obtained during the extraction. See e.g. Alain P. Foucalt. *Centrifugal Partition Chromatography*, Chromatographic Sciences Series, vol. 68, Marcel-Dekker (1995). Additionally, fractionation by FCPC, HPCPC or CCC can increase the concentration of naturally occurring antimicrobial compounds from avocados (more than 4-fold), that inhibit the growth of vegetative cells and spores of gram positive bacteria, to provide at least 1.2 to 2 times or greater antibacterial properties when compared to an acetone crude extract from avocado seed evaluated at the same concentration of solids (2.5 mg/mL).

In another embodiment of this aspect of the disclosure, the process to obtain the said enriched extract wherein the fractionation by FCPC, HPCPC or CCC said in step b) is carried out by use of a two-phases solvent system which include, but is not limited to:

methanol:heptane and/or water:hexane and/or water:butanol and/or methyl tert-butyl ether:acetonitril:water, and/or heptanes:ethyl acetate:acetonitril, heptanes:ethyl acetate:methanol:water (at different ratios) of alone or in parallel. See e.g. Alain P. Foucault, L. Chevolot. *Counter-current chromatography: instrumentation, solvent selection and some recent applications to natural product purification*. J. Chromatogr. A 808 (1998) 3-22.

In another embodiment of this aspect of the disclosure, recovered fractions comprising acetogenins with bacterial spore germination inhibiting effect said in step c) have a partition coefficient value lower than 0.5, and preferably in the in the range of between 0.19 to 0.35, when fresh seeds are used and FCPC, HPCPC or CCC is carried out with a heptane:methanol two-phase solvent system and heptane as initial stationary phase.

In another aspect of the disclosure, the extraction and purification process to obtain the enriched extract, optionally does not result in saponification of the enriched or isolated compounds. In another embodiment of this aspect of the disclosure, the extraction and purification process optionally does not result in saponification of the enriched or isolated compounds.

In another aspect of the disclosure, is the extract enriched in naturally occurring acetogenins, with antimicrobial, antibacterial or bacterial spore germination inhibiting compounds, comprised of at least one acetogenins with m/z in the range of 329 to 381, including, but is not limited to: Persenone A, Persenone B, persin or the newly discovered (2R,5E,16E)-1-acetoxy-2-hydroxy-4-oxo-nonadeca-5,16-diene or the also newly discovered (2R,16E)-1-acetoxy-2-hydroxy-4-oxo-nonadeca-16,18-diene that can be purified from *Persea* spp., or chemically synthetized to enrich the bioactivity.

In another aspect, the extract of the disclosure, enriched in naturally occurring acetogenins with antimicrobial, antibacterial or bacterial spore germination inhibiting effect is comprised of at least one compound characterized by the formula (I)

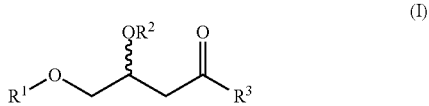

(I)

wherein:
R¹ is an acetyl group;
R² is hydrogen or a hydroxy protecting group; and
R³ is an alkenyl group with at least one carbon-carbon double bonds; and/or compounds of formula (II)

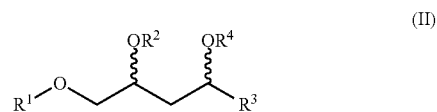

(II)

wherein:
R¹ is an acetyl group;
R² and R⁴ hydrogen or a hydroxy protecting group; and
R³ is an alkenyl group with at least one carbon-carbon double bond.

In other embodiment of this aspect of the disclosure, the hydroxy protecting group can be any known hydroxy protecting group, e.g. those described in Greene and Wuts, *Protective Groups in Organic Synthesis* (*Third Edition*), Wiley-Interscience (1999). As noted above, the compounds of formula (I) and (II) include all stereoisomeric forms which includes (R) and (S) forms and cis (Z) and trans (E) forms of the compounds. For the purposes of this disclosure, the trans (E) form can include a terminal alkene which has the formula —CH═CH₂ (see e.g. (2R,16E)-1-acetoxy-2-hydroxy-4-oxo-nonadeca-16,18-diene below).

The compounds of formula (I) can be synthesized by reacting dimethyl-1,3-dioxolane-ethylmagnesium halide (e.g. chloride or bromide) with a reagent of the formula R³COX wherein R³ is as defined above and X is a halide and subsequently forming a diol from the dioxolane ring using the procedures described in Bull et al. (1994).

Alternatively, the compounds of formula (I) can be synthesized by obtaining an unsaturated fatty acid and converting it to its corresponding methyl ketone and then reacting the corresponding methyl ketone with 2-acetoxyacetaldehye using the procedures described in MacLeod et al. (1995).

The compounds of formula (II) can be synthesized via reduction of ketone from the compounds of Formula (I) or synthesized by reacting dimethyl-1,3-dioxolane-4-ethanal with a compound of R³MgX wherein R³ is as defined above and X is a halide using procedures disclosed by Sugiyama et al. (1982).

The methods of forming the compounds of formula (I) and formula (II) are intended to be illustrative in nature and is not intended to encompass all possible means of making the compounds.

In another aspect, the extract of the disclosure is comprised of at least one compounds preferably characterized by the formula (I), and wherein there is at least one carbon-carbon double bond at the C-5 and C-6 position of the compound.

In one embodiment of this aspect of the disclosure, the said extract, comprised of at least one compounds preferably characterized by the formula (I) and wherein there is at least one carbon-carbon double bond at the C-5 and C-6 position of the compound, is characterized by having an inhibitory effect over bacterial spores from the genera which includes, but is not limited to *Clostridium, Bacillus, Alicyclobacillus* and can be used as a bacterial spore germination inhibiting agent.

In other embodiment of this aspect of the disclosure, the said extract, comprised of at least one compounds preferably characterized by the formula (I) and wherein there is at least one carbon-carbon double bond at the C-5 and C-6 position of the compound, is characterized by having an inhibitory effect over bacterial spores from the group which includes, but is not limited to *Clostridium botulinum, Clostridium perfringens, Clostridium difficile, Bacillus anthracis, Bacillus cereus, Bacillus subtilis, Bacillus lichniformis, Alicyclobacillus acidoterrestris, Alicyclobacillus acidiphilus* and can be used as an bacterial spore germination inhibiting agent.

In other embodiment of this aspect of the disclosure, the said extract is characterized by having an inhibitory effect over the genera *Listeria* at storage temperatures in the range of 0 to 10° C. and can be used as an anti-*Listeria* agent.

In another aspect, the extract of the disclosure is comprised of at least one compound preferably characterized by the formula (I), wherein there is a double bond with trans configuration at the C-16 and C-17 position of the compound.

In one embodiment of this aspect of the disclosure, the extract of the disclosure is comprised of at least one compound characterized by the formula:

(2R, 16E)-1-acetoxy-2-hydroxy-4-oxo-nonadeca-16,18-diene (2R, 5E, 16E)-1-acetoxy-2-hydroxy-4-oxo-nonadeca-5,16-diene In other embodiment of this aspect of the disclosure, the said extract is characterized by having an antibacterial, antifungical, antiviral, anti-yeast, and in spore germination inhibitory effect and can be used as an anti-microbial or spore germination inhibiting agent.

In another aspect, the extract of the disclosure can be used in compositions or products that inhibit the growth of bacterial spores, alone or in combination with other antimicrobial substances commonly known in the art which include but are not limited to nitrite compounds, nisin, bacteriocins, ethyl lauroyl arginate, essential oils, enthylenediaminetetraacetic acid (EDTA) and ascorbic acid derivatives, benzoic acid derivatives, among others in order to improve the antimicrobial activities against the growth of vegetative and sporulated states of bacteria.

In another aspect, the extract of the disclosure or compounds there in contained, or extracts derived therefrom can be used in compositions or products providing an antimicrobial, antibacterial or bacterial spore germination inhibiting effect and can be formulated in solid or oily form, with antioxidants, emulsifying agents, carriers, excipients, encapsulating agents and other formulation components to improve the application and stability of the bioactive components.

In another aspect, is the use of the extract of the disclosure to make a composition or product for providing antimicrobial, antibacterial and bacterial spore germination inhibiting effect, wherein the composition or product is selected from the group consisting of:

a pharmaceutical composition, comprising the extract and a pharmaceutically acceptable carrier;

wherein the pharmaceutical composition is suitable for one or more of the following administration vias: oral, dermal, parenteral, nasal, ophthalmical, optical, sublingual, rectal, gastrical or vaginal; Dermal administration includes topical application or transdermal administration. Parenteral administration includes intravenous, intraarticular, intramuscular, and subcutaneous injections, as well as use of infusion techniques. The extracts, compounds and compositions or products of the disclosure may be present in association with one or more non-toxic pharmaceutically acceptable ingredients to form the composition. These compositions can be prepared by applying known techniques in the art such as those taught in Remington—The Science and Practice of Pharmacy, 21st Edition (2005), Goodman & Gilman's The Pharmacological Basis of Therapeutics, 11th Edition (2005) and Ansel's Pharmaceutical Dosage Forms and Drug Delivery Systems (8th Edition), edited by Allen et al., Lippincott Williams & Wilkins, (2005).

a food additive composition comprising the extract and a food grade acceptable carrier, suitable for inclusion into food products; wherein the food product is selected from one of more of the following: fish, crustaceans, fish substitutes, crustacean substitutes, meat, meat substitutes, poultry products, vegetables, greens, sauces, emulsions, beverages, juices, wines, beers, dairy products, egg-based products, jams, jellies, grain-based products, baked goods and confectionery products;

a personal care products; wherein the personal care composition is selected from one or more of the following: creams, gels, powders, lotions, sunscreens, lipstick, body wash, herbal extracts, and formulations that support the growth of bacteria; and a cleaning composition; wherein the cleaning composition is suitable for application to one of the following: counter tops, doors, windows, handles, surgical equipment, medical tools, and contact surfaces that can contaminate humans or animals.

Another aspect of the disclosure is the use of the extracts or isolated compounds of the disclosure or compositions comprising the same, to provide an antibacterial, antimicrobial or sporicidal effect to a patient in need thereof.

Another aspect of the disclosure is the use of compositions comprising the extract of the disclosure to provide an antibacterial, antimicrobial or sporicidal effect to a pharmaceutical, food, personal care, or cleaning composition or cleaning products.

Another aspect of the disclosure is the use of the extracts or isolated compounds of the disclosure or compositions comprising the same to provide an antibacterial, antimicrobial or sporicidal effect to a surface. The effect may be produced by exposing the surface with the extracts or isolated compounds of the disclosure or by laminating or embedding the extracts or isolated compounds of the disclosure onto the surface itself.

The novel compounds from the extract and purification of the disclosure were depicted above in Formula (I). For the purposes of providing an antimicrobial, antibacterial and/or sporicidal effect, the compounds of Formula (I) can have as few as one carbon-carbon double bond for $R^3$ and this double bond can either be in the cis (Z) or trans (E) configuration. One embodiment of this scope of the compounds of Formula (I) is that the carbon-carbon double bond are at C-5/C-6, C-12/C-13, C-15/C-16, C-16/C-17 or any combination thereof, with the bonds being trans or cis bonds. Another embodiment of the scope of the compounds, include where the carbon-carbon double bond is at C-5 and C-6 alone, and/or C-16 and C-17, and/or C-12 and C-13, and/or C-15 and C-16 positions, either being trans or cis bonds.

Examples of this enhanced scope of the compounds of formula (I) include, but are not limited to:

amide of arginine monohydrochloride), nitrites or nisin (a polycyclic peptide with 34 amino acids). Use of the extracts or isolated compounds of the disclosure being a natural product or easily derived therefrom is advantageous over other known agents which are either not natural products or are not easily obtained. The use of non-natural products especially has ramifications when making food or cosmetic products which may require regulatory approval for their use.

The disclosure is further described by the following non-limiting examples which further illustrate the disclosure, and are not intended, nor should they be interpreted to, limit the scope of the disclosure.

EXAMPLES

Example 1—Antimicrobial and Sporicidal Activity of Acetone and Hexane Avocado Seed Extracts Avocado seeds were ground using a colloidal mill to obtain particles with an average radius of 0.5-2 mm. Ground avocado seeds (50 g) were mixed with either acetone or hexane at a material-to-solvent ratio of 1:2 (w/v). Mixtures

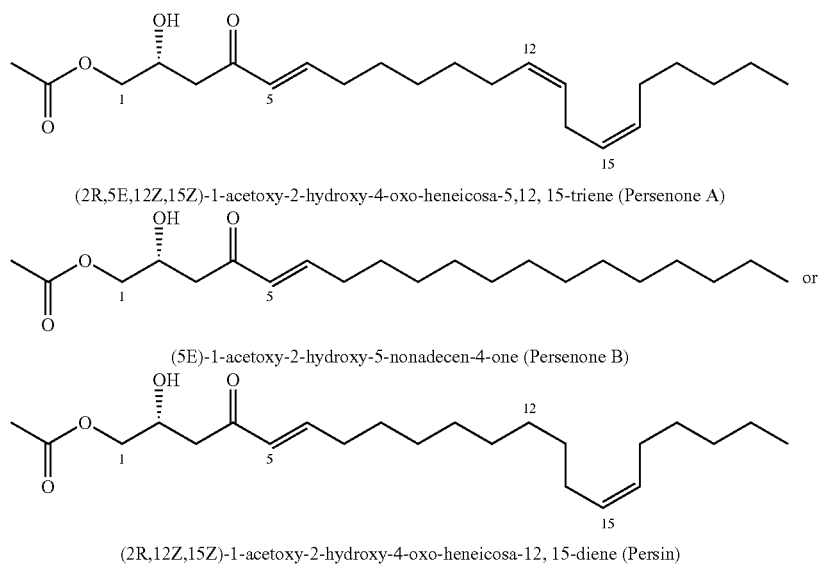

(2R,5E,12Z,15Z)-1-acetoxy-2-hydroxy-4-oxo-heneicosa-5,12, 15-triene (Persenone A)

(5E)-1-acetoxy-2-hydroxy-5-nonadecen-4-one (Persenone B)

(2R,12Z,15Z)-1-acetoxy-2-hydroxy-4-oxo-heneicosa-12, 15-diene (Persin)

Moreover, for the purposes of providing an antimicrobial, antibacterial and/or sporicidal effect, the compound of Formula (I) can be used alone or in combination with the compounds for formula (II).

Another embodiment of this aspect of the disclosure is use of the compound of formula (II) depicted below:

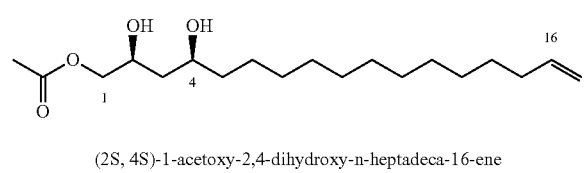 [SMILES: C=CCCCCCCCCCCC[C@H](O)C[C@H](O)COC(C)=O]

(2S, 4S)-1-acetoxy-2,4-dihydroxy-n-heptadeca-16-ene

In another aspect of the disclosure, the antibacterial, antimicrobial or spostatic/sporicidal effects are at least as effective as other known antibacterial, antimicrobial or spostatic/sporicidal agents such as LAE (ethyl ester of laurwere stored for 24 hr at 25° C. in order to obtain an avocado seed raw extract. The seed was separated from the extract by means of vacuum filtration. The raw extracts were evaporated under vacuum to dryness using a rotary evaporator (35° C., 22 in Hg) and the obtained dry matter was weighed and redissolved in acetone to a final concentration of 2.5 mg/ml. Adjusted samples were used for antimicrobial and sporicidal tests (see FIG. 1).

For the antibacterial evaluations, adjusted solutions (5 µL) were transferred to sterile 6-mm diameter discs made from Whatman no. 1 filter paper, so that after solvent evaporation each disc contained 12.5 µg of solids from the enriched avocado seed extract. Experimental controls were treated under the same conditions that the extracts and included negative control discs that contained 5 µL of acetone, and for positive control discs 5 µL of a nisin solution (30 mg/ml in sterile water) were added to provide a residual concentration of 150 µg of nisin in each disc. All test discs were left for about 1-2 hr in a Biological Safety Cabinet to evaporate the solvent. Suspensions of about 0.1 optical density (at 600 nm) containing approximately 1 to $2 \times 10^8$ CFU/ml of *Clostridium sporogenes* (ATCC 7955) vegetative cells, isolated native spores or isolated heat shocked spores were prepared as described in official protocols of Health Canada (Food Directorate, 2010). Aliquots of the suspensions (100 µL) were transferred to Petri dishes containing 15 ml of solid medium (TPGY medium) and spread evenly with a sterile plastic rod. Four discs, each containing 12.5 µg of the test extract, and two more discs (one solvent blank and one nisin positive control) were placed each dish and incubated at 37° C. under anaerobic conditions. The diameter of the inhibition zones (cm) around the discs were measured after 36 hrs.

Figure 2:
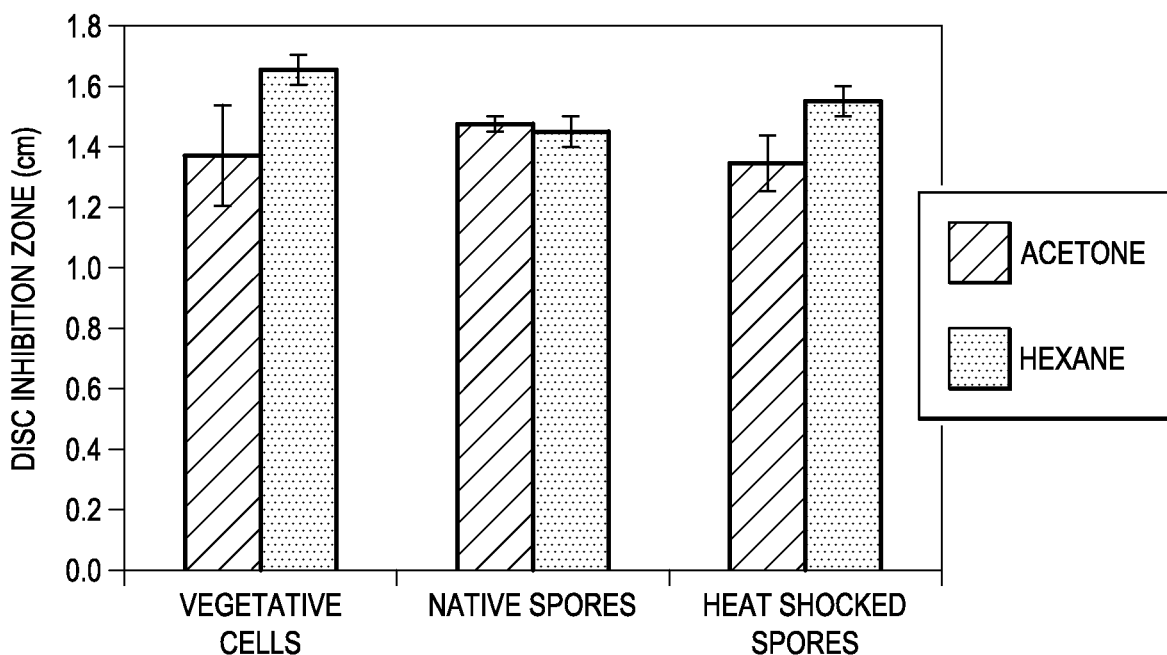
FIG. 2. Effect of the type of extraction solvent on the antimicrobial activities of crude avocado pit extracts against the growth of vegetative cells, native spores and heat shocked spores of *Clostridium sporogenes* (ATCC 7955). The extracts were tested at final concentration of 12.5 μg of solids. Data represents the average of three replications±the standard error of the mean.

Acetone and hexane avocado seed extracts showed significant antimicrobial activity against vegetative bacterial cells, as well as native and heat-shocked spores of the spore forming bacteria *Clostridium sporogenes* (see FIG. 2). Non-significant differences between the activity of acetone and hexane extracts was observed, except for heat shocked spores were the hexane extract showed around 20% higher sporicidal activity than the acetone extract. Both acetone and hexane avocado seed extracts presented higher antibacterial activities than the positive control (nisin, 150 µg). Positive control treatments (nisin) gave inhibition zones of 1.3, 1.0 and 0.9 cm for vegetative bacterial cells, spores and heat shocked spores, respectively.

Avocado seeds used to obtain the crude extracts, once ground, can be stored at temperatures below 25° C. in presence or absence of oxygen for at least 14 days without affecting the antibacterial activity against spore forming bacteria. Therefore avocado seeds can be stored as a whole or as a meal prior to the preparation of the extracts enriched in bioactive compounds.

Example 2—Specific Activity of Avocado Seed Extracts Against Vegetative Cells and Heat-Shocked Bacterial Spores of Spore-Forming Bacteria as Compared to Other Plant Sources The efficacy of the present disclosure can be observed by the preparation of crude antibacterial extracts from mango seed kernel, which has been reported in the prior art to exhibit antibacterial activity against vegetative cells of spore-forming bacteria (Kabuki et al., 2000).

Crude extracts from avocado (*Persea americana*) and mango kernel (*Mangifera indica*) were prepared as described in Example 1 and their antibacterial activities tested against the growth of vegetative cells and heat-shocked spores of *C. sporogenes* (See Table 1).

TABLE 1

Antibacterial activities of avocado seed and mango kernel extracts against vegetative cells and heat shocked spores of *Clostridium sporogenes* (ATCC 7955).

| Plant Source | Extract Concentration (mg/mL) | Antibacterial Activity against *Clostridium sporogenes* (Disc inhibition zone (cm)) | |
|---|---|---|---|
| | | Vegetative cells | Heat-shocked spores |
| Avocado Seed (*Persea americana*) | 2.5 (acetone extract) | 2.0 | 1.0 |
| | 1.25 (acetone extract) | 1.4 | 1.0 |

TABLE 1-continued

Antibacterial activities of avocado seed and mango kernel extracts against vegetative cells and heat shocked spores of *Clostridium sporogenes* (ATCC 7955).

| Plant Source | Extract Concentration (mg/mL) | Antibacterial Activity against *Clostridium sporogenes* (Disc inhibition zone (cm)) | |
|---|---|---|---|
| | | Vegetative cells | Heat-shocked spores |
| Mango Seed Kernel (*Mangifera indica*) | 100 (hexane extract) | 0.7 | 0.0 |
| | 250 (hexane extract) | 1.0 | 0.0 |
| | 100 (acetone extract) | 0.0 | 0.0 |
| | 250 (acetone extract) | 0.0 | 0.0 |
| Nisin (positive control) | 40 | 1.0 | 0.9 |
| | 2.5 | 0.0 | 0.0 |
| Methanol (negative control) | 0.0 | 0.0 | 0.0 |

Contrary to the expected only the avocado seed extracts presented activity against the two bacterial physiological stages tested herein, vegetative cells and heat shocked spores. Mango kernel extracts presented antibacterial activity against vegetative cells of spore forming bacteria but not against the growth of bacterial spores or heat-shocked spores.

The present example therefore demonstrates that the chemical nature of avocado phytochemicals is particularly useful for the inhibition of the growth of vegetative cells, spores and heat-shocked pores of spore-forming bacteria.

Example 3—Effect of Shaking on the Antimicrobial Activities of Crude Acetone and Hexane Avocado Seed Extracts Similarly to Example 1, avocado seeds were ground using a colloidal mill obtaining particles with an average diameter of 0.5-2 mm. Ground avocado seeds (50 g) were mixed with hexane at a material-to-solvent ratio of 1:2 (m/v). Mixtures were shaken or soaked at 200 rpm for 24 hr at 25° C. in order to obtain an avocado seed raw extract. The raw extracts were evaporated to dryness using a Rotary evaporator (35° C., 22 in Hg) and the obtained dry matter was weighed.

As in Example 1, dry matter was re-dissolved in acetone to a final concentration of 2.5 mg/ml for the antibacterial evaluations. *Clostridium sporogenes* (ATCC 7955) was used as test microorganism since it is a known surrogate microorganism for *Clostridium botulinum*. Antimicrobial activities against vegetative bacterial cells, as well as native and heat-shocked spores were conducted as described in Example 1.

Figure 3:
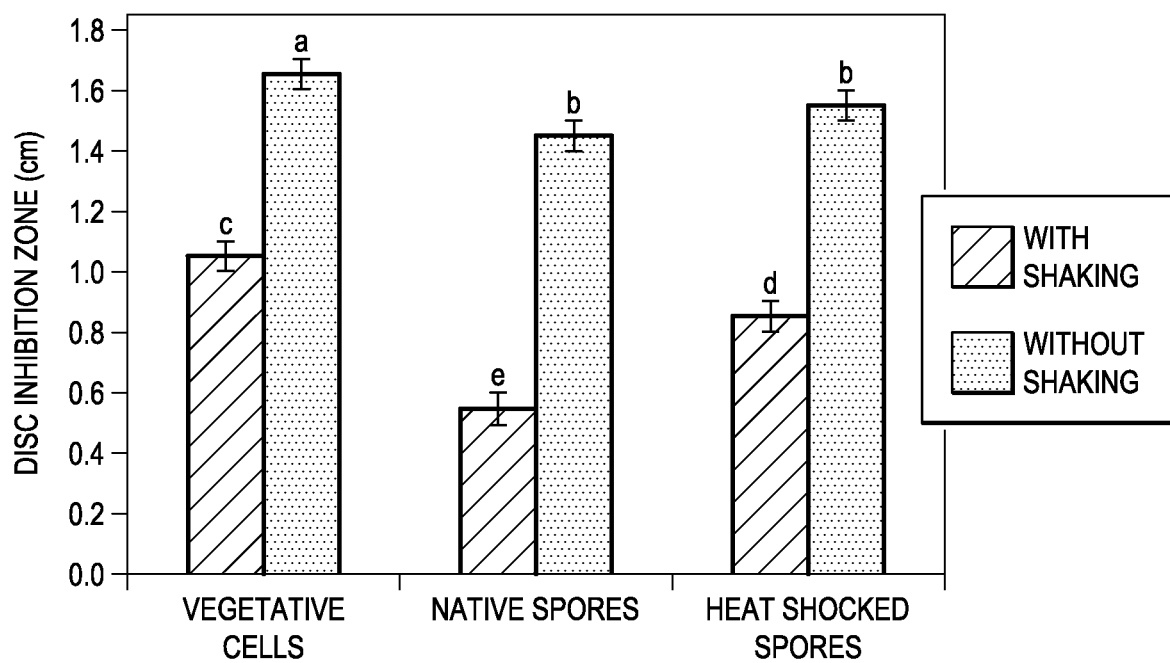
FIG. 3. Effect of shaking on the extraction of antimicrobial compounds from avocado pit extracts using hexane and evaluation of their antimicrobial activities against the growth of vegetative cells, native spores and heat shocked spores of *Clostridium sporogenes* (ATCC 7955). The extracts were tested at final concentration of 12.5 μg of solids. Data represents the average of three replications±the standard error of the mean. Values with the same letter are not significantly different (LSD test, p<0.05).

A significant effect was observed for the shaking treatment on the antimicrobial properties of the avocado seed hexane extract against vegetative bacterial cells, native spores and heat shocked spores (FIG. 3). Extracts obtained without shaking presented a higher antibacterial activity when compared with those obtained with shaking, even though the yields of extracted dry mass are higher when shaking. Through the example we can observe that shaking enhances the extraction of other non-antimicrobial compounds present in the avocado seed, therefore diluting the concentration of compounds with antibacterial activity. Therefore, the antibacterial avocado seed extract must be obtained by maceration, preferably without shaking.

Due to the dilution of compounds, the extract obtained with shaking gave similar or lower inhibition zones than the positive control (nisin, 150 µg) which showed 1.3, 1 and 0.9 cm for vegetative cells, spores and heat shocked spores, respectively.

Example 4—Effect of Extraction Time and Extraction Solvent Type (Acetone, Ethanol and Hexane) on the Antimicrobial Properties of Crude Avocado Seed Extracts Avocado seeds were ground using a colloidal mill obtaining particles with average radio of 0.5-2 mm. Ground avocado pits (50 g) were mixed with either acetone or ethanol or hexane at a material-to-solvent ratio of 1:2 (m/v). Mixtures were shaken at 200 rpm 24 hr at 35° C. in order to obtain an avocado seed crude extracts. Aliquots from each crude extract were sampled at times 0.5, 5 and 24 hr during extraction. Crude extracts obtained at different extraction times were evaporated to dryness using a Rotary evaporator (35° C., 22 in Hg) and the obtained dry matter was weighed.

Dry matter was re-dissolved in acetone to a final concentration of 2.5 mg/ml. *Clostridium sporogenes* (ATCC 7955) was used as test microorganism in the antimicrobial assays. Antibacterial activities against vegetative cells, native spores and heat shocked spores (using the disc inhibition zone determination) were conducted as described in Example 1.

Figure 4:
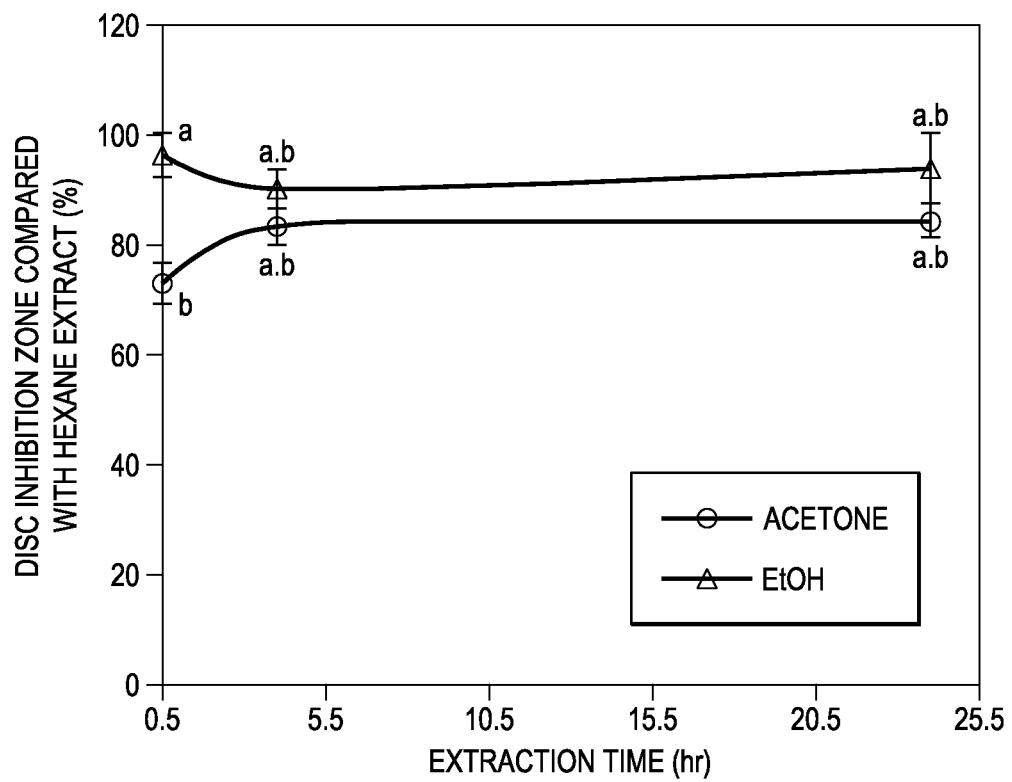
FIG. 4. Comparisons of the effect of extraction time using acetone or ethanol instead of hexane to obtain bioactive compounds from avocado pit that inhibit the growth of vegetative cells of *C. sporogenes* (ATCC 7955). The extracts were tested at final concentration of 12.5 μg of solids. Data represents the average of three replications±the standard error of the mean. Values with the same letter are not significantly different (LSD test, p<0.05).

Antimicrobial activities of hexane extracts against vegetative bacterial cells, spores and heat-shocked spores were considered as a 100% inhibition for comparison purposes with the other solvents (acetone and ethanol) at the same time interval. Results of the antibacterial activity against vegetative cells are shown in FIG. 4 and indicated that an ethanol extract obtained after an extraction time of 30 minutes had exactly the same activity as the one obtained with hexane under the same conditions. In contrast at an extraction time of 30 min with acetone the extract presented only 70% of the antimicrobial activity observed for the hexane extract, value that reached a maximum of antimicrobial activity of 80% of the activity observed in hexane extract after an extraction time of 5 hrs. Therefore this example demonstrates that since acetone and ethanol are polar solvents, increasing the extraction time at the conditions tested diluted the concentration of bioactive compounds and/or saturated the solution. Additionally and contrary to the expected, the nature of antibacterial compounds against vegetative cells of spore forming bacteria allows a better recovery using ethanol than acetone (FIG. 4).

Figure 5:
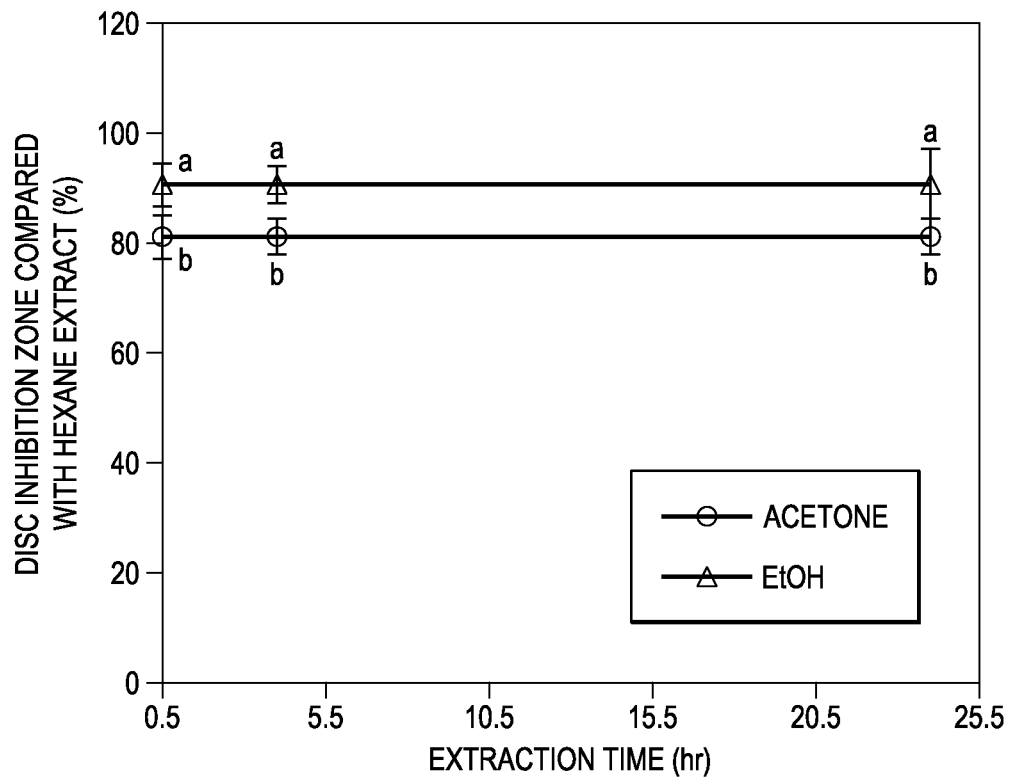
FIG. 5. Comparisons of the effect of extraction time using acetone or ethanol instead of hexane to obtain bioactive compounds from avocado pit that inhibit the growth of native spores of *C. sporogenes* (ATCC 7955). The extracts were tested at final concentration of 12.5 μg of solids. Data represents the average of three replications±the standard error of the mean. Values with the same letter are not significantly different (LSD test, p<0.05).

The results for antimicrobial properties of the extracts against native spores are presented in FIG. 5; and indicated that increases in extraction times (0.5-24 hr) did not present any differences using either solvent acetone or ethanol as the extraction solvents. Ethanol also was more selective for the extraction of the compounds with antibacterial properties against native spores.

Figure 6:
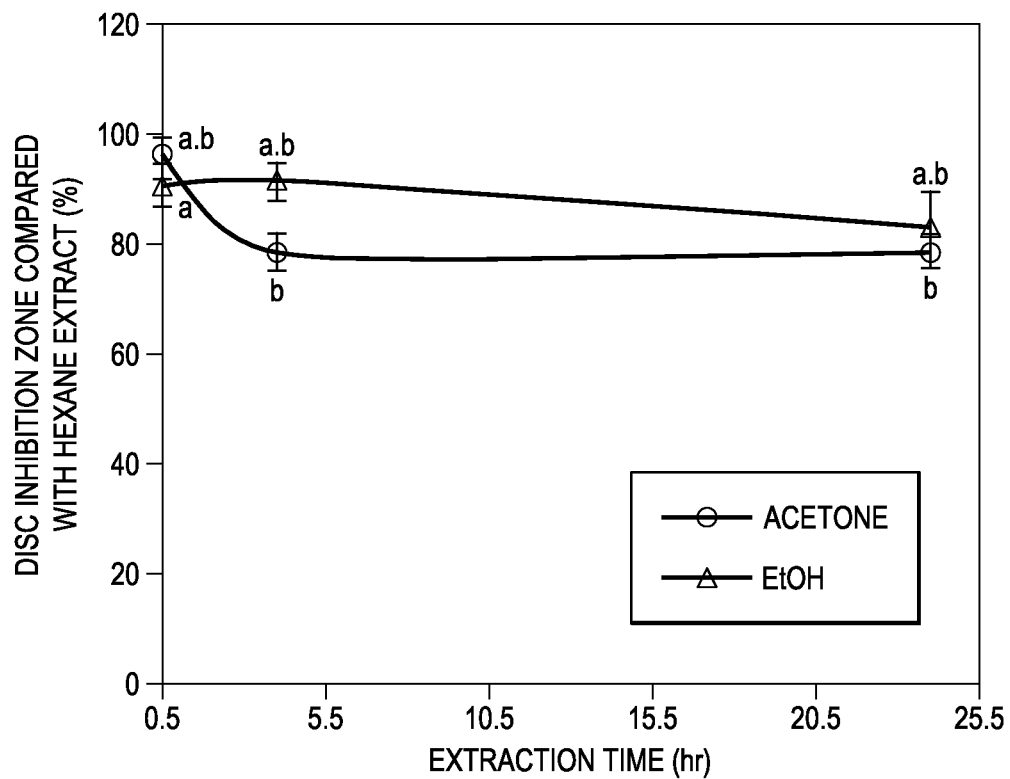
FIG. 6. Comparisons of the effect of extraction time using acetone or ethanol instead of hexane to obtain bioactive compounds from avocado pit that inhibit the growth of heat-shocked spores of *C. sporogenes* (ATCC 7955). The extracts were tested at final concentration of 12.5 μg of solids. Data represents the average of three replications±the standard error of the mean. Values with the same letter are not significantly different (LSD test, p<0.05).

Results for the antimicrobial activities of the different extracts against the growth of heat-shocked spores are presented in FIG. 6, and indicated a different trend, at 30 min of extractions both solvents (acetone and ethanol) were equally efficient for the extraction of the antibacterial molecules. However, when acetone was used as solvent over time a significant decrement on the concentrations of antibacterial molecules in the extracts was observed that varied from 100% to less than 80% bacterial inhibition for extraction times of 0.5 to 5 hr, respectively, and then the activity remained constant. Ethanol did not get as easily saturated over the extraction time with the compounds of interest as the acetone extract did and therefore, for this solvent, no differences were observed for the extraction times between 0.5 and 5 hours. Therefore the present example demonstrates that ethanol was as effective as hexane for the extraction of the antimicrobial compounds with inhibitory activities against the growth vegetative cells, native spores and heat-shocked spores from spore forming bacteria.

Figure 7A:
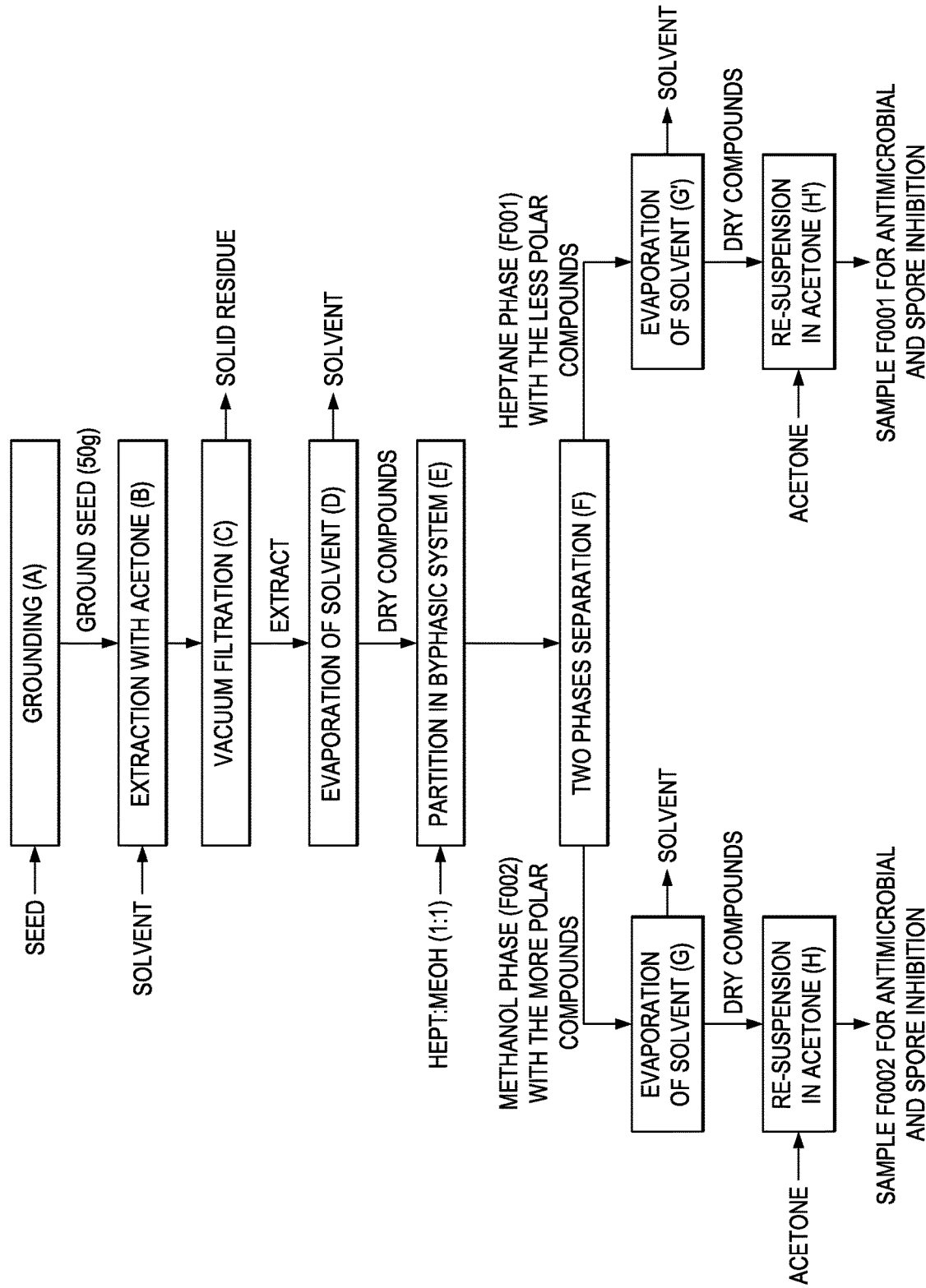
FIG. 7. A) Primary extraction diagram for the compounds present in avocado seeds using acetone and their subsequent partition in a heptane:methanol system to obtain fractions F001 and F002, in each phase respectively, later used to evaluate their antimicrobial activities against vegetative cells, native spores and heat shocked spores of gram positive bacteria. B) Simultaneous extraction and partition diagram for the compounds present in avocado seeds using a heptane:methanol system to obtain fractions F003 and F004, respectively, later used to evaluate their antimicrobial activities against vegetative cells, native spores and heat shocked spores of gram positive bacteria.

Example 5—Comparison of the Fractionation of an Acetone Avocado Seed Extract Versus Ground Avocado Seeds in Heptane: Methanol Two-Phase Non-Miscible Solvent System For the present example an acetone raw extract of avocado seed was obtained as described in Example 1, and evaporated to dryness. The dry acetone raw extract obtained from 50 g of ground avocado seeds was directly added to a separation funnel containing a two non-miscible solvent system comprised of 100 ml of heptane (upper phase F002) and 100 ml of methanol (lower phase F001) in order to allow the partition of polar and non-polar compounds contained in the extract (FIG. 7A).

Figure 7B:
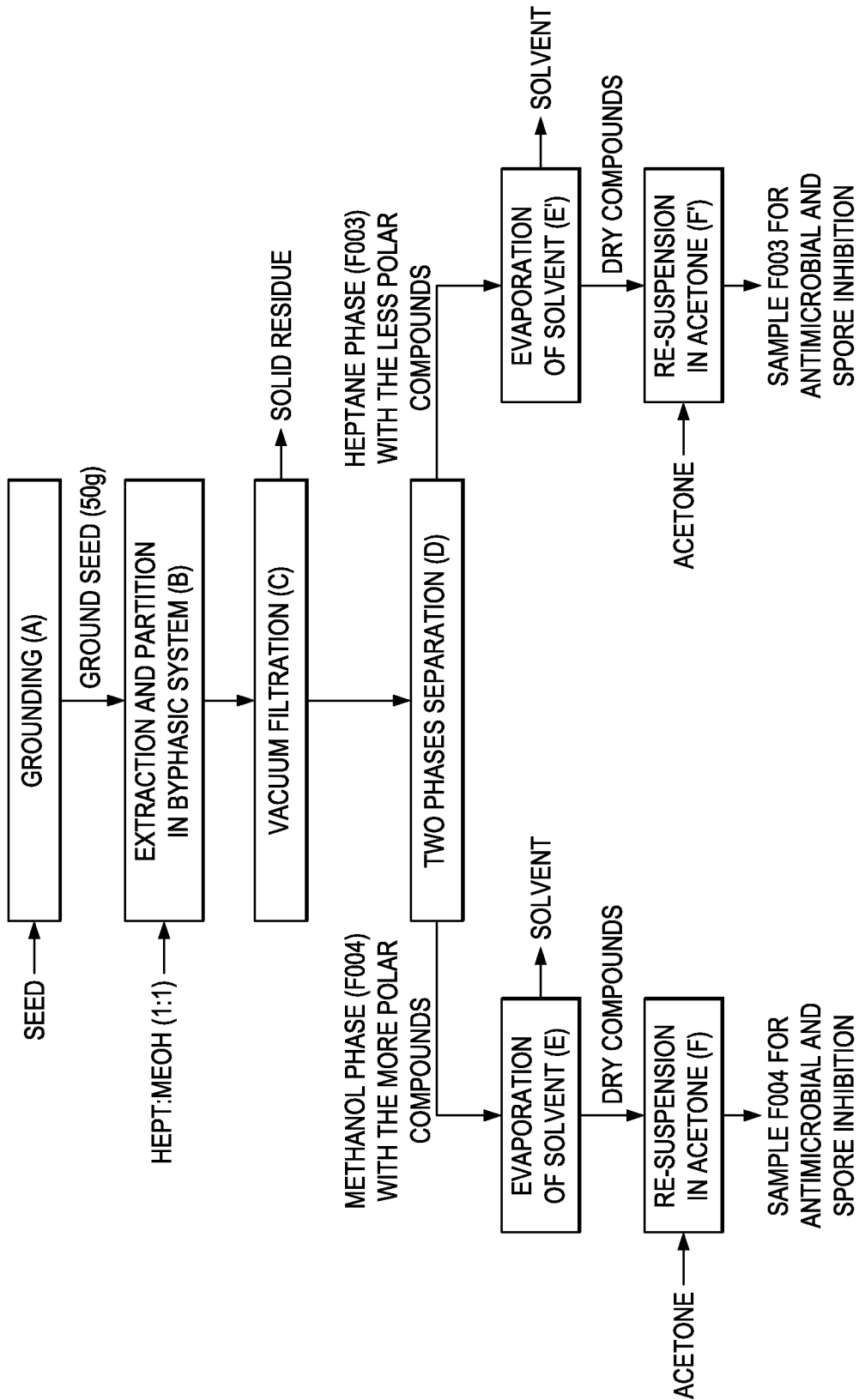

For comparison purposes a second two-phase system was prepared with 50 g of ground avocado seeds directly added the other non-miscible solvent system also comprised of 100 ml of heptane (upper phase) and 100 ml of methanol (lower phase). Mixture was shaken at 200 rpm 24 hr at 35° C. in order to selectively extract and partition the compounds present in the seed in one step. Later, the seed was separated from the extract by means of vacuum filtration. The upper (F003) and the lower (F004) phases of this system were allowed to form in a separation funnel and were collected separately FIG. 7B.

The different phases previously described (F001-F004) were evaporated to dryness individually using a rotary evaporator (35° C., 22 in Hg) and the obtained dry matter was weighed.

Dried fractions were re-dissolved in acetone to a final concentration of 2.5 mg/ml for posterior evaluation of their antibacterial activities against *Clostridium sporogenes* (ATCC 7955). Antibacterial activities against vegetative cells, native spores and heat-shocked spores (disc inhibition zone determination) were conducted as described in Example 1.

Figure 8:
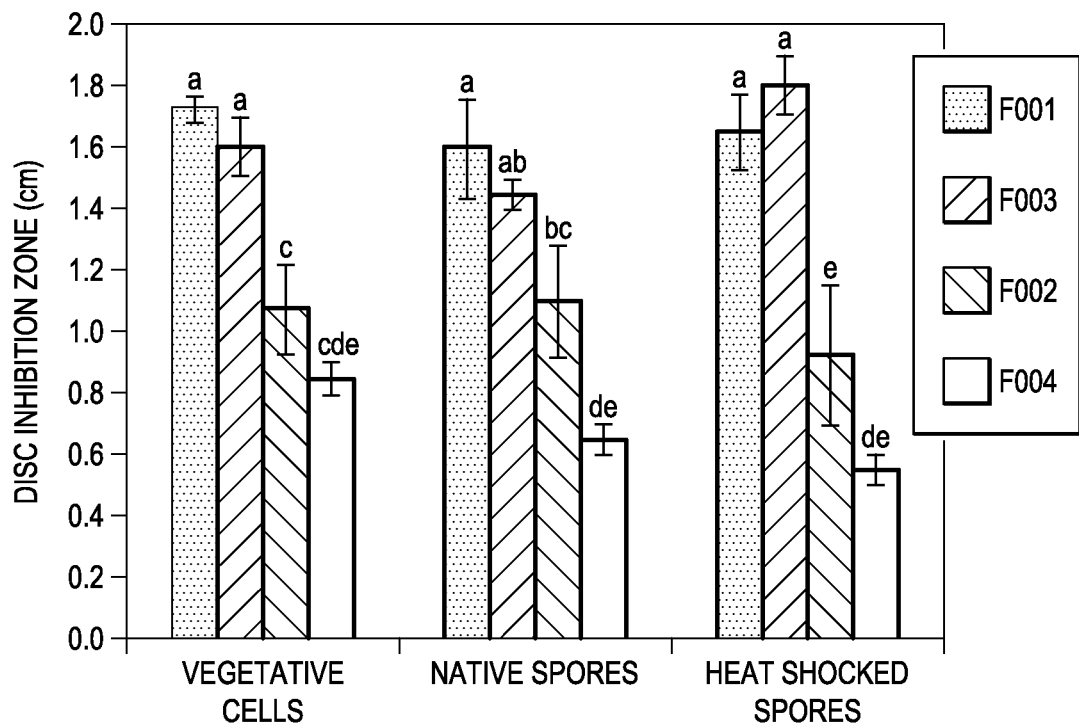
FIG. 8. Evaluation of the antimicrobial activities against the growth of vegetative cells, native spores and heat shocked spores of *Clostridium sporogenes* (ATCC 7955) of extracts F001-F004 obtained as described in FIG. 7. The extracts were tested at final concentration of 12.5 μg of solids. Data represents the average of three replications±the standard error of the mean. Values with the same letter are not significantly different (LSD test, p<0.05).

Results from the disc inhibition zones for heat shocked-spores indicated that a direct extraction of grounded avocado seeds with the two-non miscible solvents reduces the amount of contaminants that may migrate to the upper phase and that would dilute the effect of active compounds (FIG. 8), therefore illustrates that is a better option for a one step isolation of compounds that inhibit spore germination. However based on the antibacterial results for the inhibition of vegetative cells both procedures resulted in similar results with no particular benefits of one over the other one.

Figure 9:
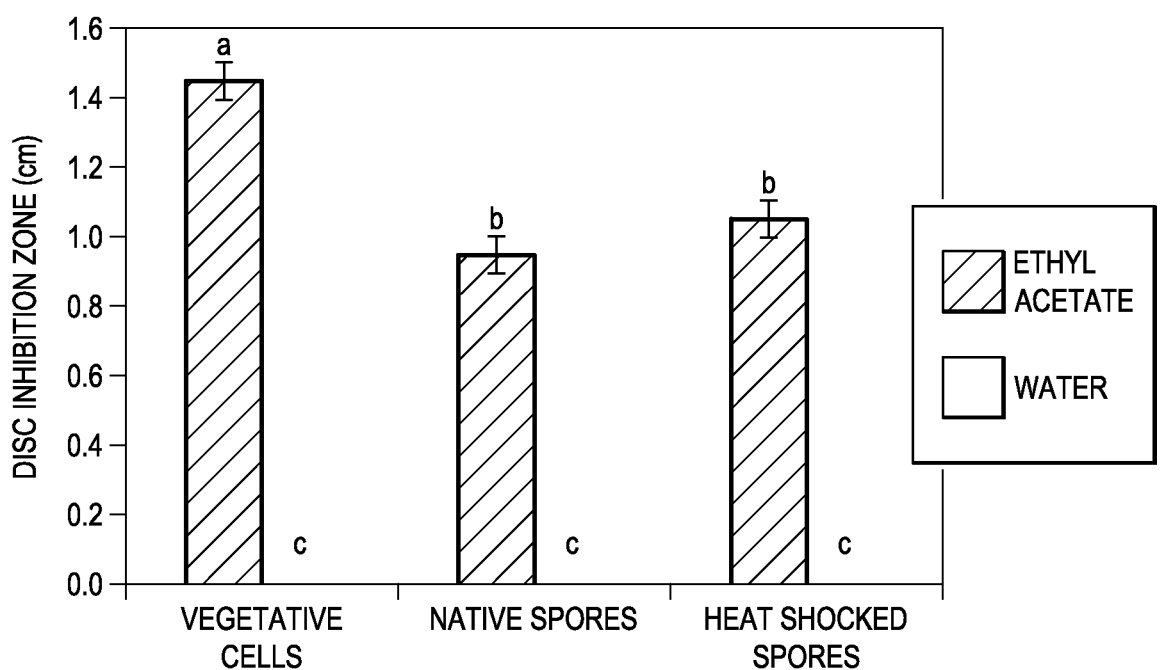
FIG. 9. Evaluation of the antimicrobial activities against the growth of vegetative cells, native spores and heat shocked spores of *Clostridium sporogenes* (ATCC 7955), of the upper and lower phases of a two phase system (ethyl acetate:water) used as a second partition of lower phase F002 (methanol) obtained as described in FIG. 7A. The extracts were tested at final concentration of 12.5 μg of solids. Data represents the average of three replications±the standard error of the mean. Values with the same letter are not significantly different (LSD test, $p<0.05$). (The letter c indicates a zero cm value for the disc inhibition zone)

The present example therefore demonstrates that the antibacterial substances were enriched in the upper phases of the heptane: methanol two-phase systems in both of the performed evaluations of direct extraction of the grounded seed and partitioning of a dried acetone avocado seed extract. However residual activity was also observed in the lower phases (F002 and F004), indicating that the upper phases were saturated with active compounds or that the compounds presented partial solubility in the lower phases of both systems. Therefore a subsequent extraction was set up by re-extracting the evaporated solids recovered from the lower methanol phase F002; the subsequent extraction systems (second two-non miscible solvent systems) used to recover the remaining antibacterial compounds were formed by ethyl acetate (100 mL) and water (100 mL). Antibacterial activities of the ethyl acetate and water phases are shown in FIG. 9. This second two-non miscible solvent systems were more polar than the first ones used and no residual antibacterial activity was found in the lower phases (mainly water).

Figure 10:
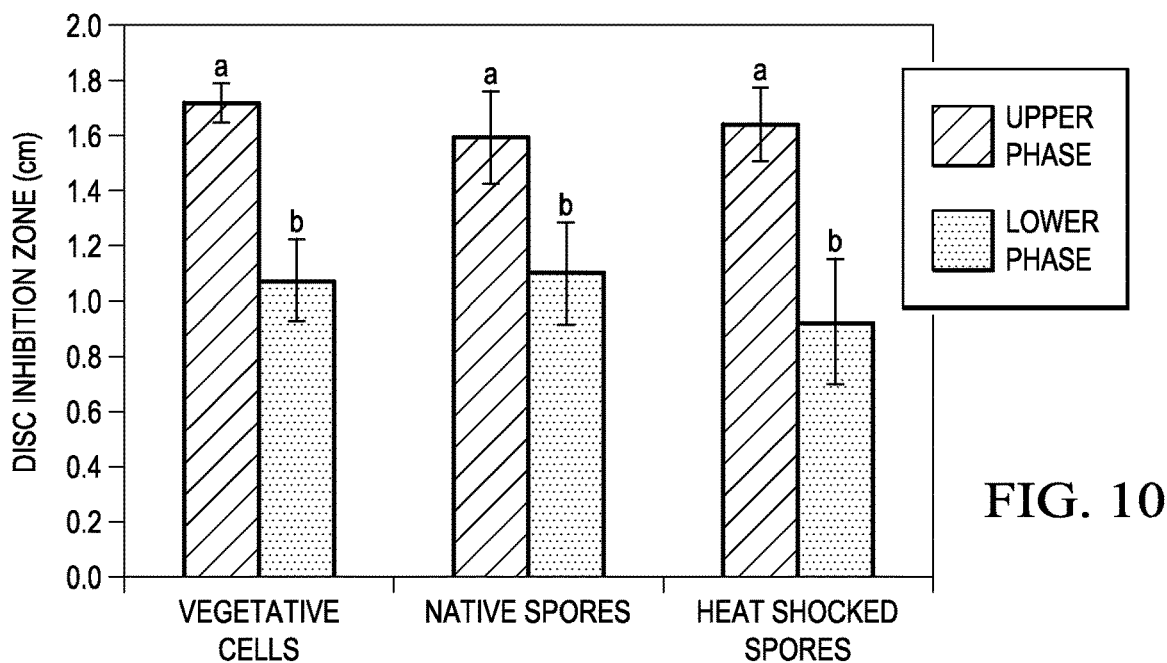
FIG. 10. Evaluation of the antimicrobial activities against the growth of vegetative cells, native spores and heat shocked spores of *Clostridium sporogenes* (ATCC 7955), of the upper and lower phases of a two phases system (hexane: methanol) used for partition of the acetonic crude extract obtained as described in Example 1. The extracts were tested at final concentration of 12.5 μg of solids. Data represents the average of three replications±the standard error of the mean. Values with the same letter are not significantly different (LSD test, $p<0.05$).

To further complete the example other two additional non-miscible solvents systems were also evaluated as alternatives, to the heptane:methanol system described above, for partitioning the dried acetone avocado seed extracts and obtaining formulations enriched in bioactive molecules. By the use of a two-phase system of hexane and methanol the antibacterial compounds were also recovered in the upper hexane phase FIG. 10. However, the heptane:methanol two-phase system proved to be more effective for the recovery of compounds in the upper phase since it presented less migration into the lower phase. Additional tests were performed by the use of aqueous two-phase systems using water, salt and ethanol to isolate the antibacterial compounds from ethanol raw extracts and the desired compounds were recovered in the upper-phase consisting mainly of ethanol.

Example 6—Effect of Saponification on the Antimicrobial Activities of Acetone and Hexane Avocado Seed Extracts Crude acetone extracts from avocado seeds were partitioned with hexane and methanol as described in Example 5. The phases were separated and the hexane rich upper phase, containing less polar compounds was evaporated to dryness using a Rotary evaporator (35° C., 22 in Hg). According to Broutin et al (2003), saponification is a necessary step to obtain a bioactive fraction that contained aliphatic or terpenic alcohols, sterols, tocopherols, carotenoids, and xanthophylls that remain in the unsaponifiable portion and are not soluble in water. However this example demonstrates that the antibacterial compounds of the present disclosure could not be obtained in the same way, indicating a different chemical nature.

Saponification of the acetone raw extract and the partitioned hexane upper phase fraction was carried out according to Broutin et al (2003), with some modifications, in order to recover the unsaponifiable portion and selectively extract the furan lipids and polyhydroxylated fatty alcohols present in them. Separately, 5 g of each extract were mixed with 2.5 ml of 12N potassium hydroxide and 10 ml of ethanol then allowed to rest for 4 hours. The aqueous-alcoholic mixture was then transferred to a separations funnel and 17.5 ml of water were added, followed by addition of 17.5 ml of dichloroethane. The mixture was shaken for 30 s and then allowed to separate into two phases. The organic phase (lower phase) was recovered. This operation was repeated 6 times, and the organic phases were combined and washed with water. The dichloroethane was evaporated to dryness using a rotary evaporator (35° C., 22 in Hg) and the obtained dry matter was weighed.

Figure 11:
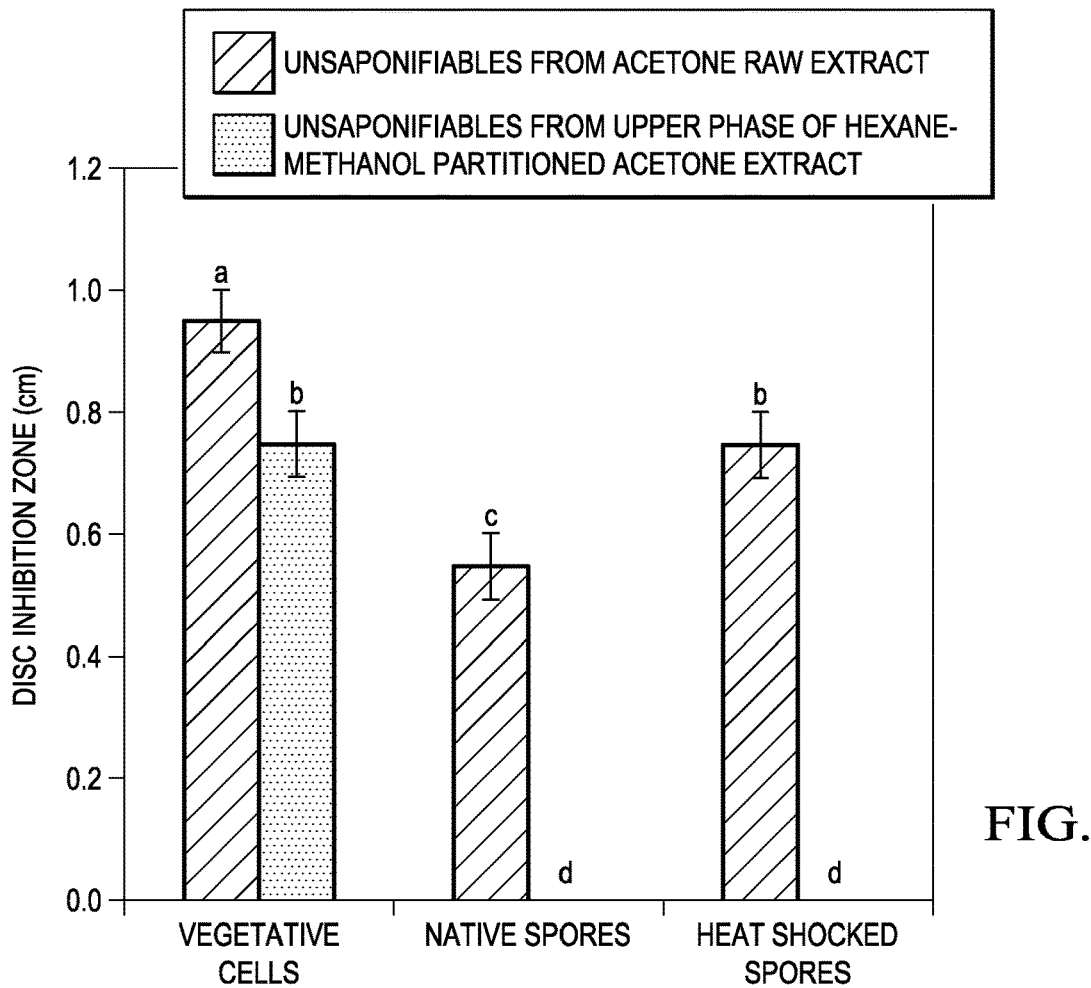
FIG. 11. Evaluation of the antimicrobial activities against the growth of vegetative cells, native spores and heat shocked spores of *Clostridium sporogenes* (ATCC 7955), of the unsaponifiables compounds from the acetone raw extract obtained as described in Example 1, and the unsaponifiables compounds from the upper phase of the two phases system (hexane:methanol) used for partition of the acetonic raw extract as described in Example 5. The extracts were tested at final concentration of 12.5 μg of solids. Data represents the average of three replications±the standard error of the mean. Values with the same letter are not significantly different (LSD test, $p<0.05$). (The letter d indicates a zero cm value for the disc inhibition zone)

Dry matter was re-dissolved in acetone to a final concentration of 2.5 mg/ml. Antimicrobial and sporicidal activity tests (disc inhibition zone determination) were conducted as described in Example 1, Clostridium sporogenes (ATCC 7955) was used as test microorganism. As shown in FIG. 11, only the unsaponifiables extracted from acetone raw extract showed disc inhibition on spores indicating that partitioning an acetone extract with hexane and methanol eliminates unsaponifiable compounds. Interestingly these unsaponifiable portion from the crude acetone extract had lower activity than the non-alkali treated crude acetone extract (FIG. 2) particularly in their inhibitory activities against the bacterial spores.

Unsaponifiable compounds in the crude acetone extract had a higher specificity for vegetative cells than for spores. Partitioning with hexane-methanol reduced the activity of unsaponifiables against vegetative cells indicating that some of these compounds could migrate to the alcoholic phase during partitioning.

When the antibacterial properties of the upper hexane and lower methanol phases, in which the unsaponifiable matter from the crude acetone extract was partitioned, were compared with the activities for crude acetone an hexane extracts described in Example 1 they were significantly lower for both phases. Results therefore indicated that active compounds are sensible to alkaline treatments or that some desirable chemical features are modified or removed during the saponification treatment and subsequent partitioning steps. Therefore, a saponification step with the aim of isolating or increasing the antimicrobial and sporicidal activity should not be considered to obtain the active avocado seed extract.

Example 7—Partitioning Chromatography of an Acetone Avocado Seed Extract

Acetone raw extract of avocado seed was obtained and evaporated to dryness as described in Example 1 then partitioned in a heptane:methanol two-phase system as described in Example 5. The upper heptane-rich phase (F001), containing less polar compounds was evaporated to dryness using a Rotary evaporator (35° C., 22 in Hg) and then injected to a Fast Centrifugal Partition Chromatographer FCPC® Bench Scale with a 1000 ml column to fractionate the chemical compounds using heptane and methanol. The heptane was pumped into the column and it served as the stationary phase (740 mL). The methanol (mobile phase) was then pumped into the column at a flow-rate of 10 mL/min. The rotor was set at 800 rpm. The concentrated extract (65 mL), obtained from the evaporated upper phase of the heptane:methanol two-phase system in which the avocado seed acetone extract was partitioned, was injected into the FCPC after the system had reached the hydrodynamic equilibrium. Methanol was used to elute fractions during the first 170 min, and after that time heptane was used as mobile phase for 100 min. The effluent from the outlet of the column was collected in test tubes using a fraction collector set at 10 ml for each tube. An aliquot of 1 ml of each fraction was collected for antibacterial and sporostatic/sporicidal activity tests. Aliquots were evaporated to dryness using a Speed Vac concentrator, the weights of the solids from each fraction were recorded and 70 pools of consecutive fractions were formed having a final concentration per pool of 2.5 mg/ml. The antibacterial properties of each pool were assessed against vegetative cells, native spores and heat-shocked spores of Clostridium sporogenes as described in Example 1. The remaining volume from each fraction (9 mL), were evaporated to dryness using a Speed Vac concentrator, stored at 80° C. and further used for chemical identification evaluations.

Figure 12:
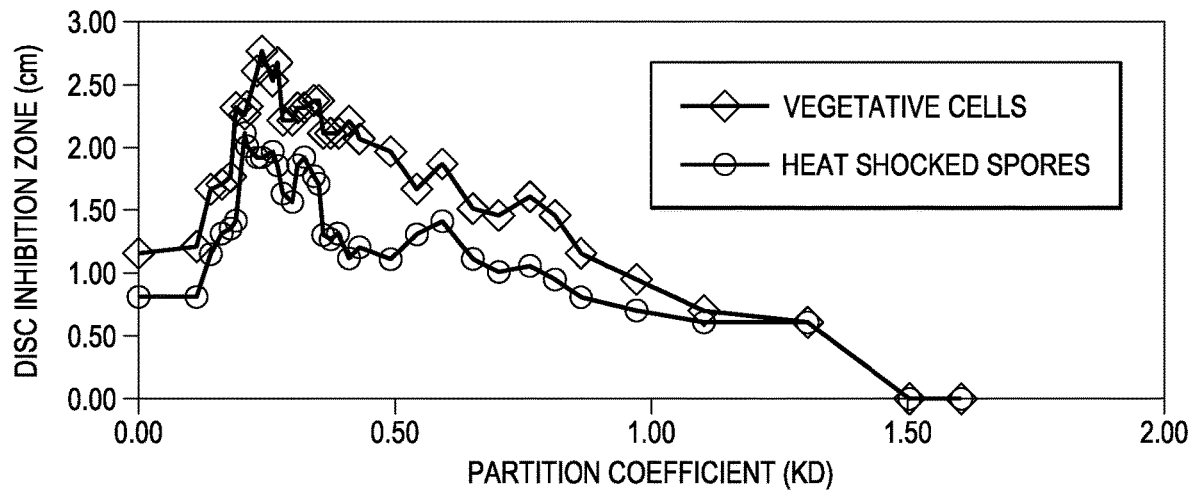
FIG. 12. Evaluation of the antimicrobial activities against the growth of vegetative cells and heat shocked spores of *Clostridium sporogenes* (ATCC 7955), of the fractions obtained by reverse phase Fast Centrifugal Partition Chromatography (RP-FCPC) of the upper phase (heptane) of the two phases system (heptane:methanol) used for partition of the acetonic raw extract as described in Example 5. The solvent system used to achieve the RP-FCPC was heptane: methanol (1:1) and methanol was used as mobile phase. The fractions were tested at final concentration of 12.5 μg of solids.

As can be observed in FIG. 12, the antibacterial activity was present in the fractions with partition coefficients (Kd) lower than 0.5 (more specifically between Kd values from 0.19 to 0.35) indicating that the active compounds were at least 2 times more soluble in heptane than in methanol. Also there was a slight difference in the activity of those fractions against vegetative cells compared to spores since inhibitors of vegetative cells growth were more spread into more polar fractions.

Partitioning the extract by FCPC increased the desired antibacterial activities (up to 3 cm diameter inhibition zones) in comparison with the previous experiments with less pure extracts, clearly indicating the need to eliminate other phytochemicals that might be diluting the concentration of the antibacterial compounds (FIG. 12). The antibacterial activities of some FCPC fractions were increased at least by 50% when compared to the data observed in FIG. 2 for the crude hexane and acetone avocado seed extracts. Results shown in FIG. 12 also demonstrate, as in FIG. 8, that the active compounds have more affinity for the heptane phase than for the methanolic phase.

In order to further characterize the antibacterial activities of the fractions with the highest activity, it was important to determine their minimum inhibitory concentration (MIC), defined as the lowest concentration of an antimicrobial that will inhibit the visible growth of a microorganism after overnight incubation. Compared to nisin, the fractions obtained by FCPC with a Kd of 0.3 and 0.4, showed a lower MIC for vegetative cells than for the native spores or heat-shocked spores of C. sporogenes (Table 2). Fraction with Kd of 0.4 was almost 2 times more active than Nisin for spore growth inhibition but fraction with Kd of 0.3 was about 15 times more active than Nisin. But in the case of heat-shocked spores, the differences between nisin and the fractions with Kd of 0.4 were less pronounced, but still presented the desired inhibitory properties against spore germination.

TABLE 2

Minimal Inhibitory Concentration (MIC) for the fractions obtained by reverse phase Fast Centrifugal Partition Chromatography (RF-FCPC) of the solids recuperated from the upper phase (heptane) of the two-phase system (heptane:methanol) used to partiton an acetonic crude avocado extract as described in Example 5.

|  | Sample tested and Partition Coefficient (Kd) | MIC (µg/ml) |
|---|---|---|
| Vegetative Cells | Nisin* | 5000 |
|  | Fraction with Kd of 0.4 | <<78 |
|  | Fraction with Kd of 0.3 | <<78 |
| Native Spores | Nisin* | 5000 |
|  | Fraction with Kd of 0.4 | >>2500 |
|  | Fraction with Kd of 0.3 | 312 |
| Heat shocked spores | Nisin* | 5000 |
|  | Fraction with Kd of 0.4 | 1250 |
|  | Fraction with Kd of 0.3 | 312 |

*Nisin was tested using initial stock solutions at 50 mg/ml and for avocado fractions at 2.5 mg/ml.

Figure 13:
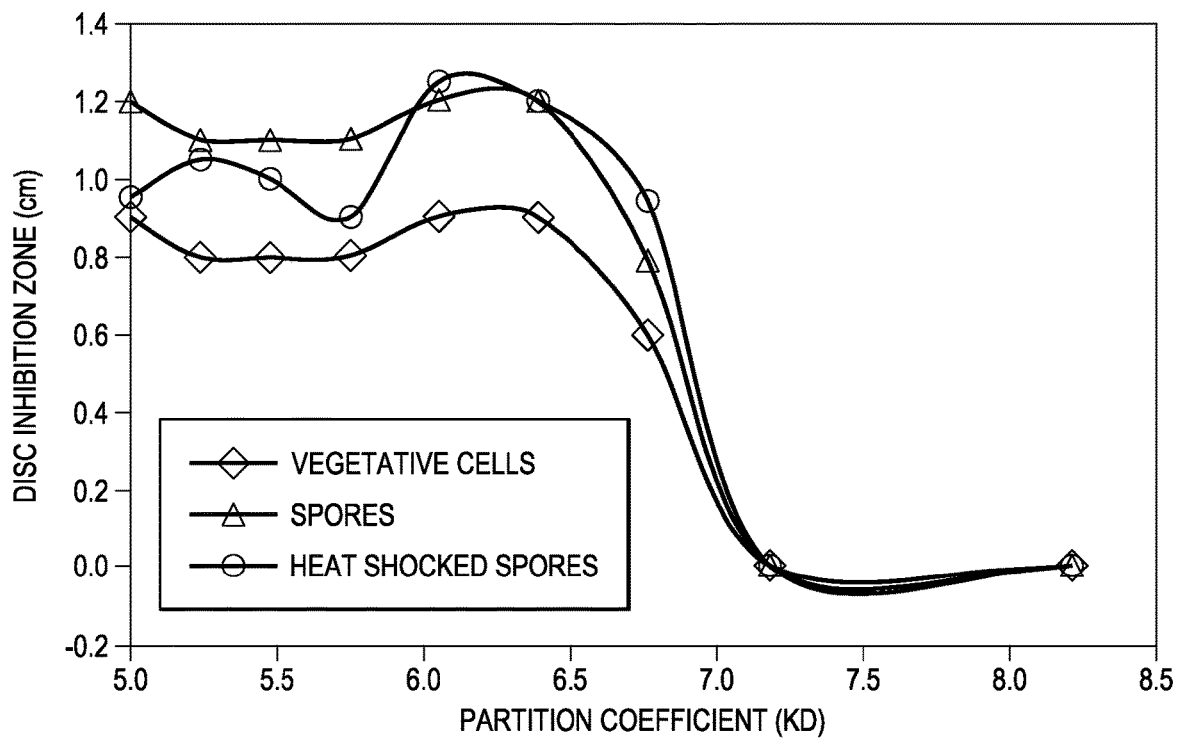
FIG. 13. Evaluation of the antimicrobial activities against the growth of vegetative cells, native spores and heat shocked spores of *Clostridium sporogenes* (ATCC 7955), of the fractions obtained by Normal phase Fast Centrifugal Partition Chromatography (NP-FCPC) of the upper phase (heptane) of the two phases system (heptane:methanol) used for partition of the acetonic raw extract as described in Example 5. The solvent system used to achieve the NP-FCPC was heptane:methanol (1:1) and heptane was used as mobile phase. The fractions were tested at final concentration of 12.5 μg of solids.

As shown in the present example, the same extract portioned by FCPC under the conditions described above (reverse phase) can also be partitioned using heptane as a mobile phase (normal phase) and results from the chromatographic separation followed the same behavior based on antibacterial activities (FIG. 13). Therefore the first fractions obtained by FCPC had better activity than the last ones (more polar) and in FIG. 13 it is shown that antibacterial activity remained present until partition coefficient reaches 7.2, indicating that other compounds that are more than 7.2 times more soluble in heptanes than methanol do not inhibit the growth of vegetative cells or spores from C. sporogenes.

Example 8—Partitioning Chromatography of Acetone Avocado Seed Extract to Obtain Fractions with Inhibitory Activities Against Other Microorganisms Besides C. sporogenes Acetone raw extract of avocado seed was obtained and evaporated to dryness as described in Example 1 then partitioned in a heptane:methanol two-phase system as described in Example 5. The upper heptane-rich phase, containing less polar compounds was evaporated to dryness using a Rotary evaporator (35° C., 22 in Hg) and then injected into a Fast Centrifugal Partition Chromatographer FCPC® using the Normal Phase conditions described in Example 7.

Figure 14:
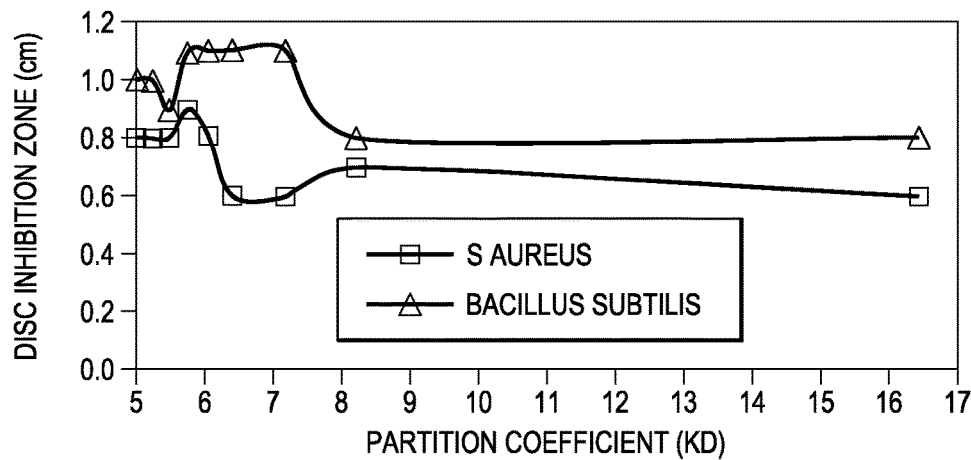
FIG. 14. Evaluation of the antimicrobial activities against the growth of vegetative cells of *S. aureus* and *B. subtilis*, of the fractions obtained by Normal phase Fast Centrifugal Partition Chromatography (NP-FCPC) of the upper phase (heptane) of the two phases system (heptane:methanol) used for partition of the acetonic raw extract as described in Example 5. The solvent system used to achieve the NP-CPC was heptane:methanol (1:1) and heptane was used as mobile phase. The fractions were tested at final concentration of 12.5 μg of solids.

The fractions obtained from Normal phase FCPC, were then used to assess their antimicrobial activities against the growth of vegetative cells from S. aureus and B. subtilis. As can be observed in FIG. 14, different compounds to the ones that are inhibiting C. sporogenes and with very low polarity are inhibiting the growth of vegetative cells of S. aureus and B. subtilis because disc inhibition zones were observed for these microorganisms when discs were inoculated with fractions of partition coefficient higher than 7, contrasting with the results of the inhibition of C. sporogenes shown in Example 7.

Table 3, summarizes the antimicrobial results from previous experiments obtained from the evaluation of the crude extracts of Example 1, extracts partitioned as described in Example 5, and unsaponifiable fractions from Example 6. As it can be observed, interestingly, they did not showed any inhibitory effects on the growth of S. aureus and very low disc inhibition zones when tested against B. subtillis in comparison with the stronger inhibitory effects observed for the enriched CPC fractions shown in FIG. 14.

TABLE 3

Evaluation of the antimicrobial activities against the growth of vegetative cells of S. aureus and B. subtilis of different crude extracts

| Fraction | S. aureus Disc inhibition zone (cm) | B. subtillis Disc inhibition zone (cm) |
|---|---|---|
| Acetone Extract | — | 0.6 |
| Hexane Extract (shaking) | — | 0.6 |
| Hexane Extract (without shaking) | — | 0.7 |
| Upper phase (hexane) of the partitioned acetone crude extract | — | 0.6 |
| Lower phase (methanol) of the partitioned acetone crude extract | — | 0.7 |

TABLE 3-continued

Evaluation of the antimicrobial activities against the growth of vegetative cells of S. aureus and B. subtilis of different crude extracts

| Fraction | S. aureus Disc inhibition zone (cm) | B. subtillis Disc inhibition zone (cm) |
|---|---|---|
| Unsaponifiable compounds from acetone extract | — | — |
| Unsaponifiable compounds from hexane-methanol partitioned acetone extract | — | — |

Example 9—Effect of High Pressure and Temperature on the Stability of Antimicrobial Activity An acetone crude extract from avocado pit was obtained and evaporated to dryness as described in Example 1. Then the acetone extracted avocado solids were partitioned into a two-phase hexane-methanol system as described in Example 5, followed by a [then] second partitioning system of ethyl acetate:water used to completely recover the active compounds present in the lower phase (methanol) phase of the first partitioning system (also described in Example 5). The hexane and the ethyl acetate phases were recovered separately and evaporated to dryness using a Rotary evaporator (35° C., 22 in Hg). Both phases were then filled in vials and exposed to high hydrostatic pressure (HHP) treatments of 300 MPa and 600 MPa (43,511 and 87,022 psi, respectively), during 3 and 6 minutes. No significant difference was observed in the antibacterial properties of the extracts after the high pressure treatments, indicating that the compounds responsible for the observed antimicrobial properties are stable to HHP treatments.

Figure 15:
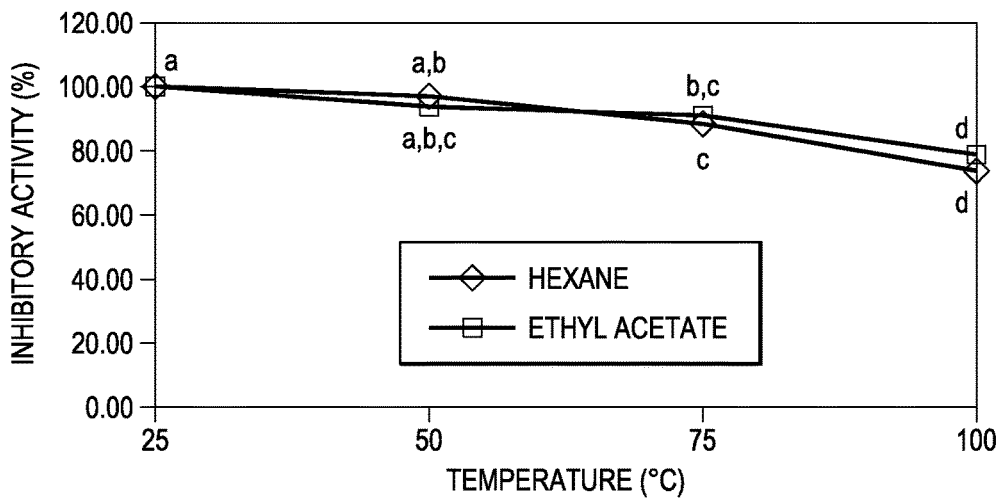
FIG. 15. Effect of temperature (25-100° C./60 min) treatments of hexane and ethyl acetate upper phases obtained as described in Example 5, on the inhibitory activity of the growth of vegetative cells of *Clostridium sporogenes* (ATCC 7955).
Figure 16:
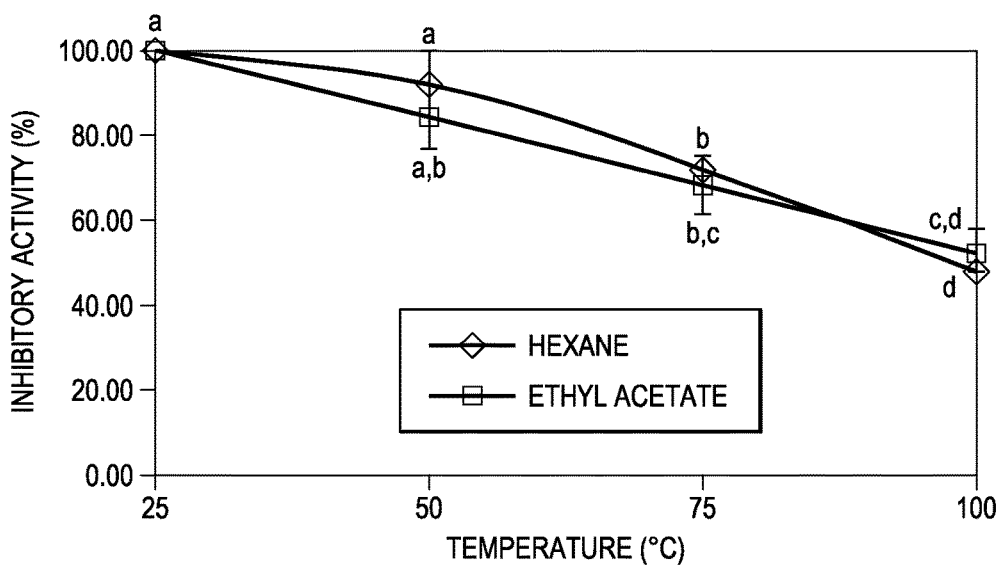
FIG. 16. Effect of temperature (25-100° C./60 min) treatments of hexane and ethyl acetate upper phases obtained as described in Example 5, on the inhibitory activity of the growth of native spores cells of *Clostridium sporogenes* (ATCC 7955).

The thermal stability of the active compounds was also tested at temperatures that ranged from 25 to 100° C. for 60 min. The compounds with activity against the growth of vegetative cells of C. sporogenes were the less sensitive to thermal treatment (FIG. 15) than those responsible for the inhibitory properties against the growth of native spores (FIG. 16). As it can be observed in FIG. 15 the inhibitory properties against vegetative cells were decreased by 20 and 23.5%, after a treatment of 100° C. for 60 minutes of the ethyl acetate and hexane extracts, respectively, and in reference to the inhibitory properties of non-heated control extracts maintained at 25° C.

Heat shocked spores were more resistant to the action of the thermally treated hexane and ethyl acetate crude extracts; the inhibitory properties against heat-shocked spores were decreased by 50%, after exposure of the extracts to 100° C. for 60 minutes, and in reference to the inhibitory properties observed for the control extracts maintained at 25° C.

Example 10—Identification of the Main Compounds Found in Bioactive Fractions

The fractions with the highest disc inhibition zones (FIG. 12), obtained by the use of reverse phase Fast Centrifugal Partition Chromatography (RP-FCPC), and that had a Kd between 0.19-0.35 were mixed together in order to form a "pool of active fractions", as described in Example 7. Initially the fractions (13) were adjusted at the same concentration of 192.3 mg/ml and equal volumes of each of them (100 μl) were taken and adjusted with ethanol to a final concentration of 50 mg/ml.

Figure 17:
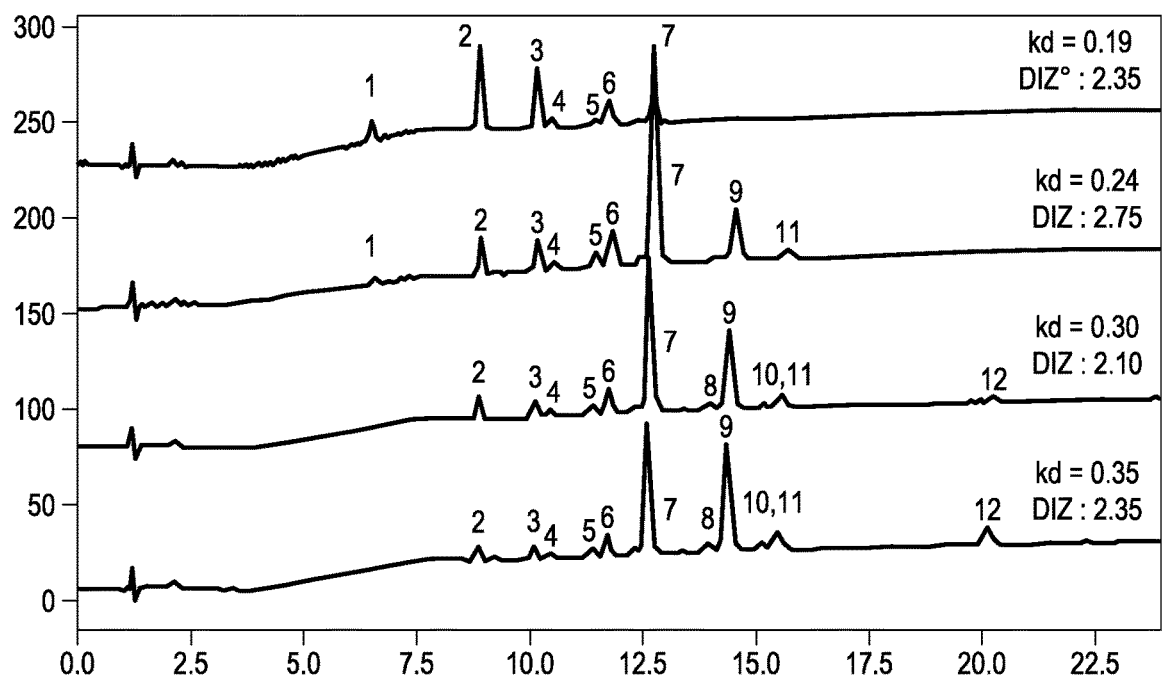
FIG. 17. Progressive change in the chromatographic profiles of the fractions present in the active pool, obtained as described in Example 10, as their partition coefficient (Kd) increases. The fractions were analyzed by means of high performance liquid chromatography and diode array detector set at 220 nm. The numbers represent the common peaks present in different fractions.

FIG. 17 shows the progressive change in the chromatographic profiles of the fractions present in the active pool, as their Kd increases. Evaporated aliquots of individual fractions were adjusted to 1 mg/ml with HPLC grade methanol and 2 μl were injected. The column used was a Zorbax Extanded-C18 (100×3 mm d.i., 3.5 μm) column. The mobile phases included water 100% as phase A and methanol 100% as phase B. The solvent gradient used is described in Table 4, pumped at a flow rate of 0.38 ml/min and a post equilibration time of 6 mins. The detector was set at a wavelength of 220 nm.

TABLE 4

Solvent Gradient used to achieve the chromatographic separation of the fractions collected after fast centrifugal partition chromatography (A = water and B = Methanol).

| Time (min) | % A | % B |
|---|---|---|
| 0 | 30 | 70 |
| 4 | 15 | 85 |
| 22 | 10 | 90 |
| 24 | 0 | 100 |
| 26 | 0 | 100 |

The typical chromatograph obtained for the active pool of antimicrobial compounds from avocado is shown in FIG. 17. The numbers indicated in the chromatogram represent the common peaks that absorb at 220 nm, labeled as Compounds 1 to 11, and the information on their mass and molecular formula is presented in Table 5. Some of these compounds have been previously reported in avocado tissues, however some of them are being disclosed herein as new chemical compounds since they were discovered by the inventors in the antimicrobial fractions. In most of the bioactive fractions, compounds such as 1, 2, 4 and 11 were in lower concentrations when compared to compounds 7 and 9 (FIG. 17).

TABLE 5

Chemical characterization of the compounds found in the antimicrobial fractions.

| Peak Number (Common name)[a] | $[M + H]^+$ Molecular Formula | Reference |
|---|---|---|
| Compound 1 | 347.2279 | None |
| Compound 2 | 349.2418 | None |
| Compound 3 | 329.2708 C19H36O4 | Néeman et al. 1970, Bittner et al. 1971 Brown 1972, Prusky et al. 1991b |
| Compound 4 | 329.2816 C19H36O4 | Kashman et al. 1969, Bittner et al. 1971, Brown 1972 |
| Compound 5 | 353.2706 C21H36O4 | None New compound |

TABLE 5-continued

Chemical characterization of the compounds found in the antimicrobial fractions.

| Peak Number (Common name)[a] | [M + H]+ Molecular Formula | Reference |
|---|---|---|
| Compound 6 | 353.2708 C21H36O4 | None New compound |
| Compound 7 (Persenone A) | 379.2864 C23H38O4 | Domergue et al., 2000, Kim et al., 2000a |
| Compound 9A (Persenone B) | 355.2865 C21H38O4 | Kim, 2000a, 2000b and 2000c |
| Compound 9B (Persin) | 381.3022 C23H40O4 | Prusky et al. 1982, Oelrichs et al., 1995 Sivanathan and Adikaram, 1989, Domergue et al., 2000 |

[a]Common name, where applicable

Example 11—Evaluation of Sporostatic and Sporicidal Activity of a Fraction Enriched in Antimicrobial Compounds In order to demonstrate that the pool of active fractions described in Example 10 (partition coefficient 0.19-0.35) had sporostatic or sporicidal activity, it was necessary to determine its minimum inhibitory concentrations (MIC) and minimum bactericidal concentrations (MBC). In general terms, MIC is defined as the lowest concentration of an antimicrobial that will inhibit the visible growth of a microorganism after overnight incubation. While the MBC is the lowest concentration of the antimicrobial that will prevent the growth of a microorganism after subculture to fresh agar media free from the antibiotic or antimicrobial agent. The pool of active the fractions was tested at concentrations ranging from 0.005 to 2.5 mg/ml and nisin was used as control.

Table 6 shows that the pool of active fractions was much better than nisin as an inhibitor of the growth of spores from *C. sporogenes* since its MIC is almost one tenth of that obtained for nisin. According to Smola (2007), if the ratio of the MBC/MIC≤4, the compound can be considered as sporocidal and if the ratio of the MBC/MIC>4, it is only sporostatic. In this example, both nisin and the pool of avocado active fractions presented a sporocidal effect.

TABLE 6

Minimum Inhibitory Concentration (MIC), Minimum Bactericidal Concentration (MBC) and MBC/MIC ratio, for nisin and the pool of active fractions isolated from avocado seed, against the growth of heat shocked spores from *C. sporogenes*.

| Sample | MIC (µg/ml) | MBC (µg/ml) | MBC/MIC[a] |
|---|---|---|---|
| Nisin | 234 | 156 | 1.5 |
| Pool of active fractions | 19.5 | 19.5 | 1 |

[a]Ratios of the MBC/MIC ≤4 indicate sporocidal activity. Ratios of the MBC/MIC >4 indicate sporostatic activity.

Example 12—Antimicrobial Activities of Isolated Chemical Compounds from Bioactive Fractions In this example, the antimicrobial activities of the same isolated compounds described in Example 10 (Table 5) were tested against the growth of vegetative cells and heat shocked spores of *C. sporogenes*, and on vegetative cells of *S. aureus, P. aeuroginosa, E. coli*. and *B. subtilis* as previously described in Example 1, and at a concentration of 0.5 mg/ml. As it can be observed in Table 7, compound 6 (peak 6) and persenone B (peak 9A) demonstrated greater antimicrobial properties when tested against *C. sporogenes*, followed by persenone A (peak 7). Additionally, from all the bioactive compounds, only persin (peak 9B) showed a lower activity than nisin, although nisin a known antimicrobial was tested at a 100-fold higher concentration. Since it has been reported that persin is able to inhibit fungi spore germination (Prusky et al., 1982), and in the present experiment it seems to have the lowest activity, it can be assumed that the other bioactive compound would have a higher activity against fungi spore.

TABLE 7

Evaluation of the antimicrobial activities of the active isolated compounds from FIG. 17 against the growth of vegetative cells and heat shocked spores of *Clostridium sporogenes* (ATCC 7955).

| | | Disc Inhibition Zone (cm) | |
|---|---|---|---|
| Peak number | Common name | Vegetative Cells | Heat Shocked Spores |
| Compound 3 | | 1.1 | 1.0 |
| Compound 5 | | 1.0 | 1.1 |
| Compound 6 | | 1.9 | 1.7 |
| Compound 7 | Persenone A | 1.6 | 1.5 |
| Compound 9A | Persenone B | 1.9 | 1.7 |
| Compound 9B | Persin | 1.0 | 0.6 |
| Negative Control | | 0.0 | 0.0 |
| Positive Control (nisin at 50 mg/ml) | | 1.1 | 1.0 |

It is important to remark that, to our surprise, all the compounds showing the highest activity against vegetative cells and heat shocked spores of *C. sporogenes* (Compound 6, Persenone B y Persenone A mentioned from the highest to the lowest antimicrobial activities reported in Table 7) contained a C5-C6 double bond (see Table 8). Moreover, if the structures of the persin (compound 9B) and persenone A (compound 7) are compared, the only difference is the lack of the C5-C6 double bond in persin (compound 9B), and in this example we demonstrate that its antimicrobial activity was reduced by 37.5%. Additionally, the only structural difference between persenone B (compound 9A) and compound 6 is that the later also presents a C16-C17 double bond, but their inhibitory activities were the same. This observation also supported the finding that a C5-C6 double is a desirable structural feature to improve the antimicrobial activities of the compounds described herein, and that the C16-C17 double bond is also a preferred structural feature, since it is the only unsaturation present in compound 3, and it had a higher activity than persin (compound 9B) that contains two instaurations and none between C16-C17.

TABLE 8

Chemical structures and common names of the compounds responsible of the antimicrobial activities of avocado seed.

| Peak/Compound Number (Common name) | Chemical structure Name |
|---|---|
| Compound 3 | 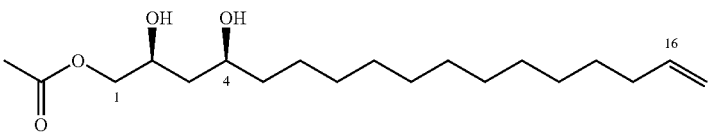 [SMILES: C=CCCCCCCCCCCC[C@H](O)C[C@H](O)COC(C)=O]<br>(2S, 4S)-1-acetoxy-2,4-dihydroxy-n-heptadeca-16-ene |
| Compound 5 | 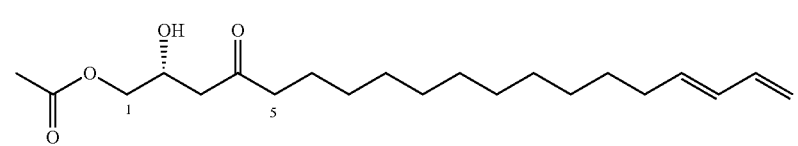 [SMILES: C=C/C=C/CCCCCCCCCCCC(=O)C[C@@H](O)COC(C)=O]<br>(2R, 16E)-1-acetoxy-2-hydroxy-4-oxo-nonadeca-16,18-diene |
| Compound 6 | 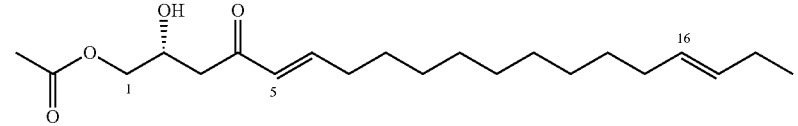 [SMILES: CC/C=C/CCCCCCCCC/C=C/C(=O)C[C@@H](O)COC(C)=O]<br>(2R, 5E, 16E)-1-acetoxy-2-hydroxy-4-oxo-nonadeca-5,16-diene |
| Compound 7 (Persenone A) | 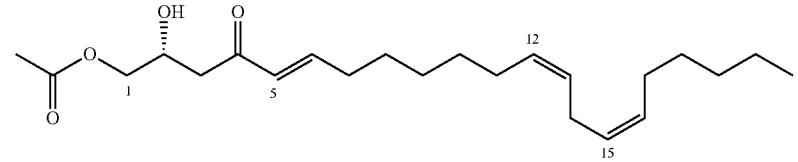 [SMILES: CCCCC/C=C\C/C=C\CCCCC/C=C/C(=O)C[C@@H](O)COC(C)=O]<br>(2R, 5E, 12Z, 15Z)-1-acetoxy-2-hydroxy-4-oxo-heneicosa-5, 12, 15-triene |
| Compound 9A (Persenone B) | 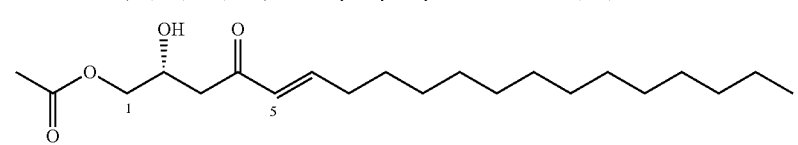<br>(5E)-1-acetoxy-2-hydroxy-5-nonadecen-4-one |
| Compound 9B (Persin) | 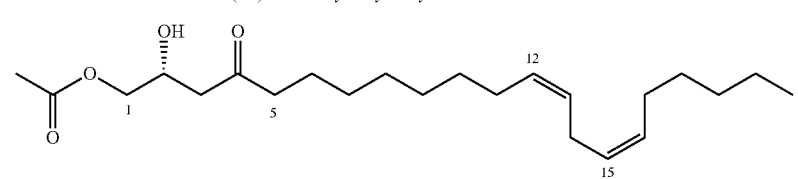<br>(R, 12Z, 15Z)-1-acetoxy-2-hydroxy-4-oxo-heneicosa-12,15-diene |

The most antibacterial compounds against *C. sporogenes* (Compound 6, Persenone B and Persenone A) did not show inhibitory activity against of *S. aureus, P. aeuroginosa* or *E. coli* (Table 9), but compound 6 also presented the greatest inhibitory activities against the growth of *B. subtillis*, followed by persenone A. Since Compound 6 is a newly discovered compound that was not previously reported as an avocado constituent, there are not previous reports of its antimicrobial or any other biological activity. Persenone A had been previously reported as antifungal but according to the results of Table 7, its antibacterial activity is specific to spore forming gram positive bacteria. The pool of active fractions obtained as described in Example 10, and that presented antibacterial properties against *C. sporogenes* in Example 10, in the present example only resulted in inhibitory properties against the spore forming bacteria *B. subtilis*.

TABLE 9

Disc inhibition zones of the bioactive compounds and the
pool of active fractions for vegetative cells and *B. Subtillis*,
*S. aureus*, *P. aeuroginosa* and *E. coli*

| Peak/Compound Number (Common name) | Antibacterial Activity (Disc inhibition zone (cm)) | | | |
|---|---|---|---|---|
| | B. Subtillis | S. aureus | P. aeuroginosa | E. coli |
| Compound 6 | 1.3 | 0.0 | 0.0 | 0.0 |
| Compound 7 (Persenone A) | 0.7 | 0.0 | 0.0 | 0.0 |
| Compound 9A (Persenone B) | 0.0 | 0.0 | 0.0 | 0.0 |
| Pool of active fractions | 0.9 | 0.0 | 0.0 | 0.0 |

The MICs for Compound 6, Persenone B (Compound 9A) and Persenone A (Compound 7) was determined against the germination of heat shocked spores from *C. sporogenes* as described in Example 11. As can be seen in Table 10, the three compounds had MICs values 15-30 fold lower than nisin, demonstrating their efficacy against bacterial spores. The MIC for the pool of active fractions was 19.5 µg/ml (Example 11) and it was reduced to 7.8 µg/ml for persenone A and persenone B when isolated, but the antimicrobial properties for Persenone B within the pool did not corresponded to its lower concentration since it contained less µg of that compound but when combined with the other bioactive molecules its activity appears to be potentiated. Interestingly, isolated compounds presented only sporostatic activity against *C. sporogenes* and did not showed the sporocidal bioactivity that was observed for the pool of active fractions (Table 6).

TABLE 10

Minimum Inhibitory Concentrations (MIC), for
nisin, Compound 6, Persenone B y A, against heat
shocked spores from *C. sporogenes*.

| Peak/Compound Number (Common name) | MIC (µg/ml) |
|---|---|
| Compound 6 | 15.6 |
| Compound 7 (Persenone A) | 7.8 |
| Compound 9A (Persenone B) | 7.8 |
| Nisin | 234 |

Example 13—Antibacterial Activities of Avocado Seed Extracts Combined with Refrigeration Temperatures for the Control of *Listeria monocytogenes*

The pool of active fractions described in Example 10 also presents antibacterial effects against cold-stressed vegetative cells of gram positive bacteria capable of growing under refrigerated conditions, such as *Listeria monocytogenes*. At the optimum growth temperature of 37° C. for *Listeria monocytogenes* the avocado pool extract enriched in bioactive acetogenins was not particularly useful for the inhibition of the growth of vegetative cells of the tested organism (Table 11). Contrary to the expected we found that the avocado seed pool extract was particularly useful for inhibiting the growth of *Listeria monocytogenes* under refrigerated conditions. Furthermore, in Table 12 we illustrate that when the antibacterial activities of the avocado acetogenins isolated in the present disclosure, were tested against the growth of vegetative cells of *Listeria monocytogenes*, the compounds presenting the desirable feature of a double bond between C5 and C6 can be used for the control of *Listeria monocytogenes* in foods and biological matrixes stored under refrigerated conditions.

TABLE 11

Antibacterial activities of avocado seed extracts combined
with low temperatures of storage against the growth of vegetative
cells of *Listeria monocytogenes*.

| Antibacterial Substance | Extract Concentration (mg/mL) | Antibacterial activity against vegetative cells of Listeria monocytogenes (Disc inhibition zone (cm)) | |
|---|---|---|---|
| | | Incubation Temperature (4° C.) Storage Time (17 days) | Incubation Temperature (37° C.) Storage Time (48 hours) |
| Avocado Seed (*Persea americana*) | 50 | 1.0 | 0.0 |
| | 25 | 1.1 | 0.0 |
| | 12.5 | 1.1 | 0.0 |
| | 6.25 | 0.0 | 0.0 |
| | 3.125 | 0.0 | 0.0 |
| Nisin (positive control) | 40 | 2.5 | 1.1 |
| Methanol (negative control) | | 0.0 | 0.0 |

TABLE 12

Antibacterial activities of the isolated avocado compounds
combined with refrigeration against the growth of vegetative
cells from *Listeria monocytogenes*.

| Peak/Compound Number (Common name) | Concentration (mg/ml) | Antibacterial Activity (Disc inhibition zone (cm)) | |
|---|---|---|---|
| | | 4° C. 20 days | 37° C. 48 hours |
| Compound 3 | 0.5 | 0.0 | 0.0 |
| Compound 5 | 0.5 | 0.0 | 0.0 |
| Compound 6 | 0.5 | 1.1 | 0.0 |
| Compound 7 (Persenone A) | 0.5 | 1.1 | 0.0 |
| Compound 9A (Persenone B) | 0.5 | 1.0 | 0.0 |
| Compound 9B (Persin) | 0.5 | 0.0 | 0.0 |
| Nisin (positive control) | 40 | 2.6 | 1.1 |
| MeOH (negative control) | | 0.0 | 0.0 |

Figure 18:
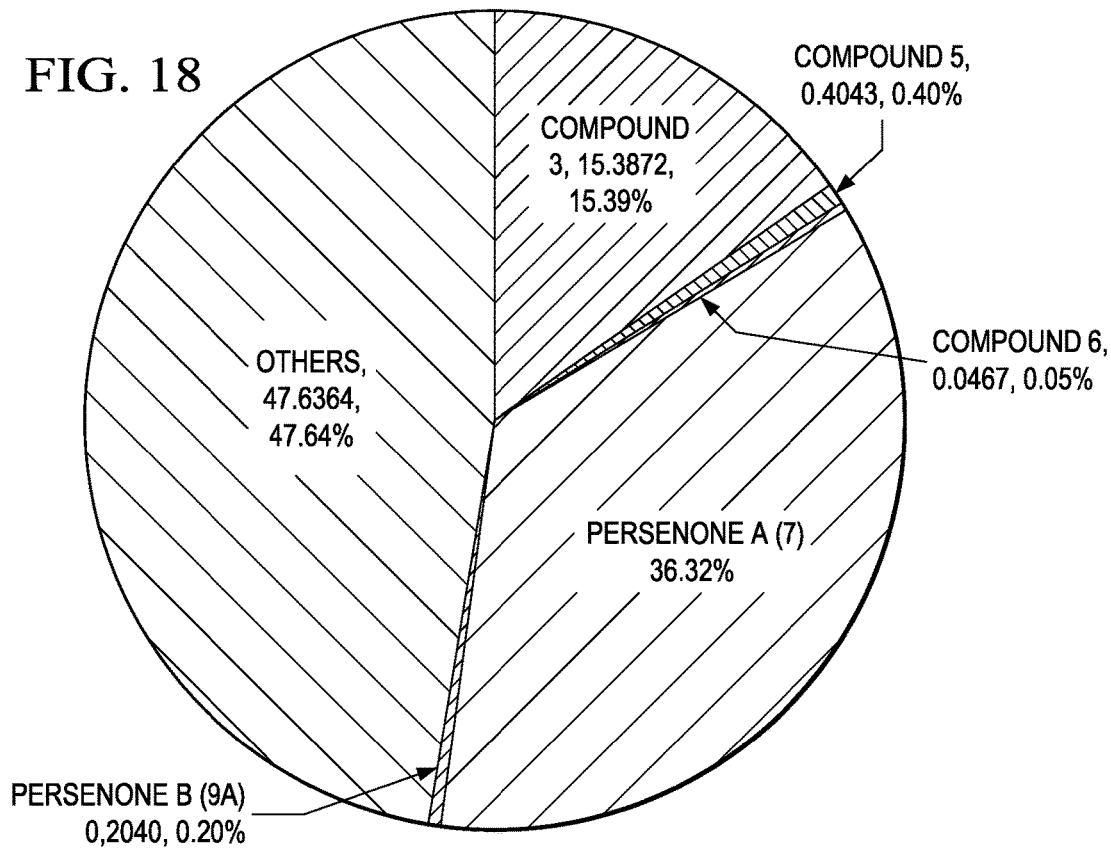

Example 14—Quantification of the Antimicrobial Compounds in Enriched Avocado Extracts The concentration of the antibacterial compounds present in the pool of active fractions described in Table 7 (Example 10) is presented in FIG. 18. Persenone A represents 36.32% of the dry weight of the pool of active fractions, persenone B was only 0.20% and compound 6 accounts for the lowest amount (0.05%). It seems that the other components in the mixture do not affect the inhibitory activity of Persenone A, and therefore no further purification may be needed.

Table 13 shows that there is a very similar concentration of the most bioactive compounds against *C. sporogenes* (Compound 6, Persenone B and Persenone A) in fresh avocado pulp and seed, being Persenone A the most concentrated. The information of this example is relevant because if the bioactive compounds are also present on the pulp they can be easily obtained from other parts of the fruit. The present example also demonstrates that humans are being exposed to the bioactive molecules, when eating the fruit, at the concentrations required for achieving their antibacterial properties; therefore establishing their commercial potential in the food, medical and cosmetic arts.

TABLE 13

Concentrations of Compound 6, Persenone B and Persenone A in fresh avocado pulp and seed (ug/g of fresh weight).

| Compound | Avocado Pulp (ug/g of fresh weight) | Avocado Seed (ug/g of fresh weight) |
|---|---|---|
| Compound 6 | 18.59 ± 2.30 | 19.11 ± 3.45 |
| Compound 7 (Persenone A) | 74.86 ± 4.75 | 63.32 ± 6.34 |
| Compound 9A (Persenona B) | 42.42 ± 10.22 | 31.89 ± 2.87 |

Having thus described in detail various embodiments of the present disclosure, it is to be understood that the disclosure defined by the above paragraphs is not to be limited to particular details set forth in the above description as many apparent variations thereof are possible without departing from the spirit or scope of the present disclosure.

LIST OF LITERATURE REFERENCES

Adikaram, N. K. B., Ewing, D. F., Karunaratne, A. M., Wijeratne, E. M. K. 1992. Antifungal compounds from immature avocado fruit peel. Phytochemistry. 31:93-96.

AOAC Official Method 966.04 Sporicidal Activity of Desinfectants. Revised 2002.

Baratta et al. 1998. Chemical composition, antimicrobial and antioxidant activities of laurel, sage, rosemary, oregano and coriander essential oils. J. Essent. Oil Res. 10(6): 618-627.

Beltran, J. B. U. and Bonaventura, J. S. Use of cationic preservative in food products. U.S. Pat. No. 7,862,842 B2. Jan. 4, 2011.

Bevilacqua, A., Sinigaglia, M., Corbo, M. R. 2008. *Alicyclobacillus acidoterrestris*: New methods for inhibiting spore germination. International Journal of Food Microbiology. 125:103-110.

Bittner, S., Gazit, S., Blumenfeld, A. 1971. Isolation and identification of a plant growth inhibitor from avocado. Phytochemistry, 10(7):1417-1421

Blackburn, P., Gusik, S A., Polak, J., Rubino, S. D., Nisin compositions for use as enhanced, broad range bactericides. U.S. Pat. No. 5,217,950. Jun. 8, 1993.

Brown, B. I. 1972. Isolation of Unpleasant Flavor Compounds in the Avocado (*Persea americana*). J. Agr. Food Chem. 20:753-757.

Bull, S. D and Carman, R. M. Synthesis of the Avocado Antifungal, (Z,Z)-2-hydroxy-4-oxohenicosa-12,15-dien-1-yl acetate. Aust. J. Chem., 1994, 47, pp. 1661-1672.

Burt. S. 2004. Essential oils: their antibacterial properties and potential applications in foods—a review. International Journal of Food Microbiology. 94:223-253.

Chang, C. F., Isogai, A., Kamikado, T., Murakoshi, S., Sakurai, A., Tamura, S. Isolation and structure elucidation of growth inhibitors for silkworm larvae from avocado leaves. Agr. Biol. Chem, 1975, 39 (5), pp. 1167-1168.

Chia, T. W. R., Dykes, G. A. 2010. Antimicrobial activity of crude epicarp and seed extracts from mature avocado fruit (*Persea Americana*) of three cultivars. Pharmaceutical Biology 48(7):753-756.

Deans, S. G., Ritchie, G. 1987. Antibacterial properties of plant essential oils. International Journal of Food Microbiology. 5:165-180.

Domergue, F., Helms, G. L., Prusky, D., Browse, J. 2000. Antifungal compounds from idioblast cells isolated from avocado fruits. Phytochemistry 54: 183-189.

Food Directorate, 2010. *Clostridium botulinum* challenge testing of ready-to-eat foods. Food Directorate Health Products and Food Branch. Health Canada. Version Number 1, Issue: Nov. 24, 2010.

Hashimura H, Ueda C, Kawabata J, Kasai T. 2001. Acetyl-CoA carboxylase inhibitors from avocado (*Persea americana* Mill.) fruits. Biosci Biotechnol Biochem. 65:1656-1658.

Jensen, Lloyd B. 1951. Process for extraction of antibiotic material. U.S. Pat. No. 2,550,254. SWIFT & CO. United States.

Kabuki, T., Nakajima, H., Arai, M., Ueda, S., Kuwabara, Y., Dosako, S. 2000. Characterization of novel antimicrobial compounds from mango (*Magnifera indica* L.) kernel seeds. Food Chem. 71:61-66.

Kashman, Y., Néeman, I. and Lifshitz, A. 1969. New Compounds from Avocado Pear. Tetrahedron. 25:4617-4631.

Kim, O. K., Murakami, A., Nakamura, Y., Takeda, N., Yoshizumi, H., Ohigashi, H. 2000a. Novel nitric oxide and superoxide generation inhibitors, persenone A and B, from avocado fruit. Journal of Agricultural and Food Chemistry 48 (5), pp. 1557-1563.

Kim, O. K., Murakami, A., Nakamura, Y., Kim, H. W., Ohigashi, H. 2000b. Inhibition by (−)-Persenone A-related Compounds of Nitric Oxide and Superoxide Generation from Inflammatory Leukocytes. Bioscience, Biotechnology and Biochemistry 64 (11), pp. 2500-2503.

Kim, O. K., Murakami, A., Takahashi, D., Nakamura, Y., Torikai, K., Kim, H. W., Ohigashi, H. 2000c. An Avocado Constituent, Persenone A, Suppresses Expression of Inducible Forms of Nitric Oxide Synthase and Cyclooxygenase in Macrophages, and Hydrogen Peroxide Generation in Mouse Skin. Bioscience, Biotechnology and Biochemistry 64 (11), pp. 2504-2507.

King, W., Ming, X. Antibacterial composition for control of gram positive bacteria in food applications. U.S. Pat. No. 6,620,446B2. Sep. 16, 2003.

Kobiler, I., Prusky, D., Midland, S., Sims, J. J., Keen, N. T. 1993. Compartmentation of antifungal compounds in oil cells of avocado fruit mesocarp and its effect on susceptibility to *Colletotrichum gloeosporioides*. Physiol. Mol. Plant Pathol. 43: 319-328.

Maseko, R. B. 2006. Synthesis of authentic organic standards of antibacterial compounds isolated from avocados. Master of Science Thesis. Tshwane University of Technology, South Africa.

MacLeod, J. K. and Schaeffler, L. A Short Enantioselective Synthesis of a Biologically Active Compound from *Persea Americana*. J. Nat. Prod., vol. 58., no. 8, pp. 1270-1273 (August 1995).

Monticello, D. J. Control of microbial growth with lantibiotic/lysozyme formulations. U.S. Pat. No. 5,458,876. Oct. 17, 1995.

Murakoshi, S., Isogai, A., Chang, C. F., Kamikado, T., Sakurai, A., Tamura, S. The effects of two components from avocado leaves (*Persea americana* Mill.) and related compounds on the growth of silkworm larvae. *Bombyx mori* L. Nippon Oyo Dobutsu Konchu Gakkaishi 1976; 20:87-91.

NCCLS M100-S12: Performance Standards for Antimicrobial Susceptibility Testing: Twelfth Informational Supplement (ISN 1-56238-454-6).

Néeman, I., Lifshitz, A., Kashman, Y. 1970. New antibacterial agent isolated from the avocado pear. Applied microbiology, 470-473.

Oberlies, N. H., Rogers, L. L., Martin, J. M. and McLaughlin, J. L. 1998. Cytotoxic and Insecticidal Constituents of the Unripe Fruit of *Persea americana*. J. Nat. Prod. 61:781-785.

Oelrichs, P. B., Ng, J. C., Seawright, A. A., Ward, A., Schaffeler, L., MacLeod, J. K. 1995. Isolation and identification of a compound from avocado (*Persea americana*) leaves which causes necrosis of the acinar epithelium of the lactating mammary gland and the myocardium. Natural Toxins, 3(5):344-349

Perumalla, A. V. S., Hettiarachchy, N. S. 2011. Green tea and grape seed extracts—Potential applications in food safety and quality. Food Research International. 44(4): 827-839.

Prusky, D., Keen, N. T., Sims, J. J., Midland, S. L., 1982. Possible involvement of an antifungal diene in the latency of *Colletotrichum gloeosporioides* on unripe avocado fruits. Phytopathol. 72 (12), 1578.

Prusky, D., Plumbley, R. A., Koliber, I., 1991a. Modulation of natural resistance of avocado fruits to *Colletotrichum gloeosporioides* by CO2. Plant Pathol. 40, 45.

Prusky, D., Koliber, I., Fishman, Y., Sims, J. J., Midland, S. L., Keen, N. T., 1991b. Identification of an Antifungal Compound in Unripe Avocado Fruits and its Possible Involvement in the Quiescent Infections of *Colletotrichum gloeosporioides*. J. Phytopathol. 132, 319.

Ramos-Jerz, M. D. Phytochemical analysis of avocado seeds (*Persea americana* Mill., c.v. Hass). [Ph. D. Dissertation], Gottingen, Alemania, 2007. Technishen Universität Brauschweig.

Rayman, M. K. 1981. Nisin: a possible alternative or adjunct to nitrite in the preservation of meats. Applied and Environmental Microbiology. 41(2):375-380.

Rodriguez-Carpena, J. G., Morcuende, D., Andrade, M. J., Kylli, P. and Estévez, M. 2011. Avocado (*Persea americana* Mill.) phenolics, in vitro antioxidant and antimicrobial activities and inhibition of lipid and protein oxidation in porcine patties. J. Agric. Food Chem. 59:5625-5635.

Rodriguez-Saona, C., Millar, J. G., Trumble, J. T. 1997. Growth inhibitory, insecticidal, and feeding deterrent effects of (12Z,15Z)-1-acetoxy-2-hydroxy-4-oxo-heneicosa-12,15-diene, a compound from avocado fruit, to *Spodoptera exigua*. Journal of Chemical Ecology, 23(7): 1819-1831

Seawright A. A., Oelrichs P. B., Ng, J. C., MacLeod J. K., Ward, A., Schaffeler, L., Carman, R. M. 1995. Method of treatment of cancer as well as method of inhibition of lactition in mammals. Patent Coop. Treaty Int. Appl. No WO 95/22969, Australian National University, Australia.

Sivanathan, S., Adikaram, N. K. B., 1989. Biological Activity of Four Antifungal Compounds in Immature Avocado. Journal of Phytopathology, 125(2): 97-109

Smola, M. 2007. Contribution à l'étude de la formulation et de l'analyse physicochimique de formulations pédiatriques microémulsionnées. [Docteur in Sciences Pharmaceutiques]. Universite Louis Pasteur Strasbourg. France.

Sugiyama, T., Sato, A. and Yamashita, K. Synthesis of all four stereoisomers of antibacterial component of avocado. Agric. Biol. Chem., 46(2), 481-485 (1982).

Tang, Y., Shi, Y., Zhao, W., Hao, G. and Le, G. 2008. Inhibition of Food-Borne Pathogens by T1, a Novel Antimicrobial Peptide as a Potential Food Preservative. International Journal of Food Engineering. Vol 4, Iss. 4, Art, 14. p. 1-19.

Ugbogu, O. C. & Akukwe, A. R. 2009. The antimicrobial effect of oils from *Pentaclethra macrophylla* Bent, *Chrysophyllum albidum* G. Don and *Persea gratissima* Gaerth F on some local clinical bacteria isolates. African Journal of Biotechnology, 8(2): 285-287.

Pollack S, Perez A, Plattner K. 2010. Fruit and tree nuts outlook. Economic Research Service. United States Department of Agriculture USDAFTS-341/Mar. 26, 2010.

Valeri, A., and N. Gimeno. 1954. Phytochemical and toxicological study of pericarp of the avocado pear. Rev. Med. Vet. Parasitol (Maracay) 13:37.

Wilhoit, D. Film and method for surface treatment of foodstuffs with antimicrobial compositions. U.S. Pat. No. 5,573,797. Nov. 12, 1996.

Wilhoit, D. Antimicrobial composition for surface treatment of foodstuffs. U.S. Pat. No. 5,573,800. Nov. 12, 1996.

Wilhoit, D. Surface treatment of foodstuffs with antimicrobial compositions. U.S. Pat. No. 5,573,801. Nov. 12, 1996.

Yang, H., Li, X., Tang, Y., Zhang, N., Chen, J. and Cai, B. 2009. Supercritical fluid CO2 extraction and simultaneous determination of eight annonaceous acetogenins in Annona genus plant seeds by HPLC-DAD method. J Pharm Biomed Anal. 49:140-144.

What is claimed is:

1. A method of inhibiting bacterial spore germination on or in a product, said method comprising:

providing an isolated inhibitor compound of the formula:

wherein:

R is selected from the group consisting of H and $C_{1-6}$ alkyl,

A is selected from the group consisting of O and OH, n is 0 or 1, and m is 0 or 1; and selecting a product having bacterial spores on or in the product; and applying the isolated inhibitor compound on or in the selected product to inhibit bacterial spore germination on or in the product.

2. The method of claim 1, wherein the inhibitor compound has the formula:

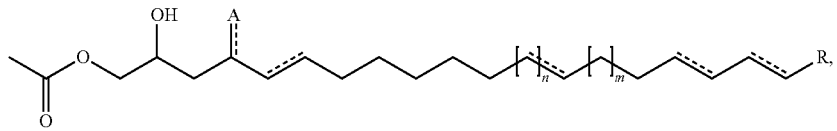

wherein:
R is selected from the group consisting of H and $C_{1-6}$ alkyl;
A is selected from the group consisting of O and OH;
n is 0 or 1; and
m is 0 or 1.

3. The method of claim 1, wherein the inhibitor compound has the formula:

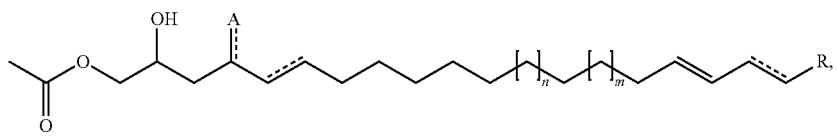

wherein:
R is selected from the group consisting of H and $C_{1-6}$ alkyl;
A is selected from the group consisting of O and OH;
n is 0 or 1; and
m is 0 or 1.

4. The method of claim 1, wherein the inhibitor compound has the formula:

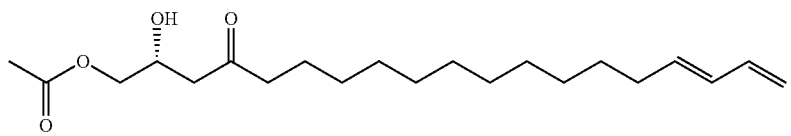

5. The method of claim 1, wherein the inhibitor compound has the formula:

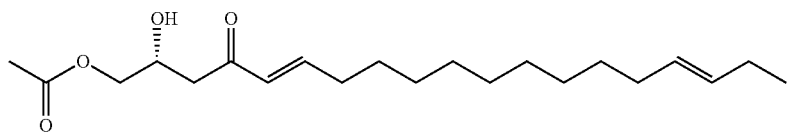 [SMILES: CC/C=C/CCCCCCCCC/C=C/C(=O)C[C@@H](O)COC(C)=O]

6. The method of claim 1, wherein the method is carried out to inhibit germination of bacterial spores selected from the group consisting of *Clostridium, Bacillus, Alicyclobacillus*, and combinations thereof.

7. The method of claim 1, wherein the method is carried out to inhibit germination of bacterial spores selected from the group consisting of *Clostridium botulinum, Clostridium perfringens, Clostridium difficile, Bacillus anthracis, Bacillus cereus, Bacillus subtilis, Bacillus lichinformis, Alicyclobacillus acidoterrestris, Alicyclobacillus acidophilus*, and combinations thereof.

8. The method of claim 1, wherein the method is carried out to inhibit germination of heat shocked bacterial spores.

9. The method of claim 1, wherein the product is a food product.

10. The method of claim 9, wherein the food product is selected from the group consisting of fish, crustaceans, fish substitutes, crustacean substitutes, meat, meat substitutes, poultry products, vegetables, greens, sauces, emulsions, beverages, juices, wines, beers, dairy products, egg-based products, jams, jellies, grain-based products, baked goods, confectionery products, and combinations thereof.

11. The method of claim 9, wherein the food product is a ready to eat food product stored under refrigerated conditions.

12. The method of claim 1, wherein the product is a personal care product.

13. The method of claim 12, wherein the personal care product is selected from the group consisting of creams, gels, powders, lotions, sunscreens, lipstick, body wash, herbal extracts, formulations that support the growth of bacteria, and combinations thereof.

14. The method of claim 1, wherein the product is a surface to be treated.

15. The method of claim 14, wherein the surface to be treated is selected from the group consisting of counter tops, doors, windows, handles, surgical equipment, medical tools, contact surfaces that can contaminate humans or animals, and combinations thereof.

16. The method of claim 1, wherein the inhibitor compound is applied as a component of a composition, said composition further comprising:
a carrier.

17. The method of claim 16, wherein the composition further comprises:
an antimicrobial substance selected from the group consisting of nitrite compounds, nisin, bacteriocins, ethyl lauroyl arginate, ethylene diaminetetraacetic acid compounds, ascorbic acid compounds, benzoic acid compounds, and combinations thereof.

18. The method of claim 16, wherein the inhibitor compound in the composition is applied at a concentration of at least about 7.8 μg/ml.

19. A method of inhibiting bacterial spore germination on or in a subject, said method comprising:

providing an isolated inhibitor compound of the formula

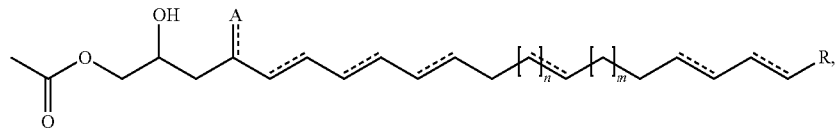

wherein:

R is chosen from the group consisting of H and $C_{1-6}$ alkyl,

A is chosen from the group consisting of O and OH, n is 0 or 1, and m is 0 or 1; and selecting a subject having bacterial spores on or in the subject's body; and administering to the selected subject the isolated inhibitor compound in an amount effective to inhibit bacteria spore germination on or in the subject.

20. The method of claim 19, wherein the inhibitor compound has the formula:

wherein:

R is selected from the group consisting of H and $C_{1-6}$ alkyl;

A is selected from the group consisting of O and OH;

n is 0 or 1; and m is 0 or 1.

21. The method of claim 19, wherein the inhibitor compound has the formula:

wherein:

R is selected from the group consisting of H and $C_{1-6}$ alkyl;

A is selected from the group consisting of O and OH;

n is 0 or 1; and m is 0 or 1.

22. The method of claim 19, wherein the inhibitor compound has the formula:

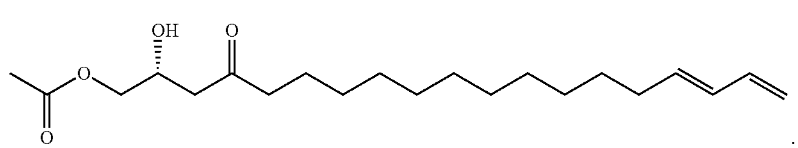 [SMILES: C=C/C=C/CCCCCCCCCCCC(=O)C[C@@H](O)COC(C)=O]

.

23. The method of claim 19, wherein the inhibitor compound has the formula:

[chemical structure]

24. The method of claim 6, wherein the method is carried out to inhibit germination of bacterial spores selected from the group consisting of *Clostridium, Bacillus, Alicyclobacillus*, and combinations thereof.

25. The method of claim 19, wherein the method is carried out to inhibit germination of bacterial spores selected from the group consisting of *Clostridium botulinum, Clostridium perfringens, Clostridium difficile, Bacillus anthracis, Bacillus cereus, Bacillus subtilis, Bacillus lichinformis, Alicyclobacillus acidoterrestris, Alicyclobacillus acidophilus*, and combinations thereof.

26. The method of claim 19, wherein said administering is carried out orally, dermally, parenterally, nasally, opthalmically, optically, sub-lingually, rectally, gastricly, vaginally, or using combinations thereof.

27. The method of claim 19, wherein the inhibitor compound is applied as a component of a composition, said composition further comprising:
a pharmaceutical carrier.

28. The method of claim 27, where the composition further comprises an antimicrobial substance selected from the group consisting of nitrite compounds, nisin, bacteriocins, ethyl lauroyl arginate, ethylene diaminetetraacetic acid compounds, ascorbic acid compounds, benzoic acid compounds, and combinations thereof.

29. The method of claim 27, wherein the inhibitor compound in the composition is administered at a concentration of at least about 7.8 μg/ml.

30. A method of inhibiting bacterial spore germination on or in a product, said method comprising:
providing an isolated inhibitor compound of the formula:

[chemical structures] or ;

and
applying the isolated inhibitor compound on or in the product to inhibit bacterial spore germination on or in the product.

31. The method of claim 30, wherein the method is carried out to inhibit germination of bacterial spores selected from the group consisting of *Clostridium, Bacillus, Alicyclobacillus*, and combinations thereof.

32. The method of claim 30, wherein the method is carried out to inhibit germination of bacterial spores selected from the group consisting of *Clostridium botulinum, Clostridium perfringens, Clostridium difficile, Bacillus anthracis, Bacillus cereus, Bacillus subtilis, Bacillus lichinformis, Alicyclobacillus acidoterrestris, Alicyclobacillus acidophilus*, and combinations thereof.

33. The method of claim 30, wherein the method is carried out to inhibit germination of heat shocked bacterial spores.

34. The method of claim 30, wherein the product is a food product.

35. The method of claim 34, wherein the food product is selected from the group consisting of fish, crustaceans, fish substitutes, crustacean substitutes, meat, meat substitutes, poultry products, vegetables, greens, sauces, emulsions, beverages, juices, wines, beers, dairy products, egg-based products, jams, jellies, grain-based products, baked goods, confectionery products, and combinations thereof.

36. The method of claim 34, wherein the food product is a ready to eat food product stored under refrigerated conditions.

37. The method of claim 30, wherein the product is a personal care product.

38. The method of claim 37, wherein the personal care product is selected from the group consisting of creams, gels, powders, lotions, sunscreens, lipstick, body wash, herbal extracts, formulations that support the growth of bacteria, and combinations thereof.

39. The method of claim 30, wherein the product is a surface to be treated.

40. The method of claim 39, wherein the surface to be treated is selected from the group consisting of counter tops, doors, windows, handles, surgical equipment, medical tools, contact surfaces that can contaminate humans or animals, and combinations thereof.

41. The method of claim 30, wherein the inhibitor compound is applied as a component of a composition, said composition further comprising:
a carrier.

42. The method of claim 41, wherein the composition further comprises:
an antimicrobial substance selected from the group consisting of nitrite compounds, nisin, bacteriocins, ethyl lauroyl arginate, ethylene diaminetetraacetic acid compounds, ascorbic acid compounds, benzoic acid compounds, and combinations thereof.

43. The method of claim 41, wherein the inhibitor compound in the composition is applied at a concentration of at least about 7.8 µg/ml.

* * * * *

UNITED STATES PATENT AND TRADEMARK OFFICE
CERTIFICATE OF CORRECTION

PATENT NO. : 10,575,521 B2
APPLICATION NO. : 15/148712
DATED : March 3, 2020
INVENTOR(S) : Hernandez-Brenes et al.

It is certified that error appears in the above-identified patent and that said Letters Patent is hereby corrected as shown below:

On the Title Page

Item (73), Line 1, delete "TECHNOLOGICO" and insert --"TECNOLOGICO"-- in its place.

In the Claims

At Column 41, Line 12, delete "6" and insert --19-- in its place.

Signed and Sealed this
Thirtieth Day of June, 2020

Andrei Iancu
*Director of the United States Patent and Trademark Office*